US010435430B2

(12) United States Patent
Prakash et al.

(10) Patent No.: US 10,435,430 B2
(45) Date of Patent: *Oct. 8, 2019

(54) METHODS AND COMPOUNDS USEFUL IN CONDITIONS RELATED TO REPEAT EXPANSION

(71) Applicants: Ionis Pharmaceuticals, Inc., Carlsbad, CA (US); Board of Regents of the University of Texas System, Austin, TX (US)

(72) Inventors: Thazha P. Prakash, Carlsbad, CA (US); Jiaxin Hu, Coppell, TX (US); Jing Liu, Austin, TX (US); Dongbo Yu, Austin, TX (US); David Corey, Dallas, TX (US); Eric E. Swayze, Encinitas, CA (US)

(73) Assignees: IONIS PHARMACEUTICALS, INC., Carlsbad, CA (US); THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/908,429

(22) PCT Filed: Jul. 31, 2014

(86) PCT No.: PCT/US2014/049197
§ 371 (c)(1),
(2) Date: Jan. 28, 2016

(87) PCT Pub. No.: WO2015/017675
PCT Pub. Date: Feb. 5, 2015

(65) Prior Publication Data
US 2016/0159846 A1    Jun. 9, 2016

Related U.S. Application Data

(60) Provisional application No. 62/019,820, filed on Jul. 1, 2014, provisional application No. 61/860,823, filed on Jul. 31, 2013.

(51) Int. Cl.
*C12N 15/113* (2010.01)
*C07H 21/02* (2006.01)

(52) U.S. Cl.
CPC ........... *C07H 21/02* (2013.01); *C12N 15/113* (2013.01); *C12N 2310/11* (2013.01); *C12N 2310/32* (2013.01); *C12N 2320/34* (2013.01)

(58) Field of Classification Search
CPC .. C07H 21/02; C12N 15/113; C12N 2310/11; C12N 2310/32; C12N 2320/34
See application file for complete search history.

(56) References Cited

U.S. PATENT DOCUMENTS

| 3,687,808 A | 8/1972 | Merigan et al. |
| 4,845,205 A | 7/1989 | Huynh Dinh et al. |
| 5,130,302 A | 7/1992 | Spielvogel et al. |
| 5,134,066 A | 7/1992 | Rogers et al. |
| 5,175,273 A | 12/1992 | Bischofberger et al. |
| 5,367,066 A | 11/1994 | Urdea et al. |
| 5,432,272 A | 7/1995 | Benner |
| 5,457,187 A | 10/1995 | Gmelner et al. |
| 5,459,255 A | 10/1995 | Cook et al. |
| 5,484,908 A | 1/1996 | Froehler et al. |
| 5,502,177 A | 3/1996 | Matteucci et al. |
| 5,525,711 A | 6/1996 | Hawkins et al. |
| 5,552,540 A | 9/1996 | Haralambidis |
| 5,587,469 A | 12/1996 | Cook et al. |
| 5,594,121 A | 1/1997 | Froehler et al. |
| 5,596,091 A | 1/1997 | Switzer |
| 5,614,617 A | 3/1997 | Cook et al. |
| 5,645,985 A | 7/1997 | Froehler et al. |
| 5,681,941 A | 10/1997 | Cook et al. |
| 5,750,692 A | 5/1998 | Cook et al. |
| 5,763,588 A | 6/1998 | Matteucci et al. |
| 5,830,653 A | 11/1998 | Froehler et al. |
| 6,005,096 A | 12/1999 | Matteucci et al. |
| 6,268,490 B1 | 7/2001 | Imanishi et al. |
| 6,525,191 B1 | 2/2003 | Ramasamy |
| 6,670,461 B1 | 12/2003 | Wengel et al. |
| 6,770,748 B2 | 8/2004 | Imanishi et al. |
| 6,794,499 B2 | 9/2004 | Wengel et al. |
| 7,034,133 B2 | 4/2006 | Wengel et al. |

(Continued)

FOREIGN PATENT DOCUMENTS

| WO | WO 1999/014226 | 3/1999 |
| WO | WO 2004/106356 | 12/2004 |

(Continued)

OTHER PUBLICATIONS

Ostergaard et al. Nucleic Acid Research 41: 9634-9650 (Year: 2013).*

(Continued)

*Primary Examiner* — Brian Whiteman
(74) *Attorney, Agent, or Firm* — Parker Highlander PLLC

(57) ABSTRACT

Described are compounds and methods useful for the treatment and investigation of diseases and disorders associated with expanded repeat-containing RNA molecules. In certain embodiments, compounds and methods useful for the modulation of ATXN-3 pre-mRNA are described. In certain embodiments, compounds and methods useful for the modulation of ATN-1 mRNA are described.

17 Claims, 5 Drawing Sheets
Specification includes a Sequence Listing.

(56) References Cited

U.S. PATENT DOCUMENTS

| | | | |
|---|---|---|---|
| 7,053,207 B2 | 5/2006 | Wengel | |
| 7,399,845 B2 | 7/2008 | Seth et al. | |
| 7,427,672 B2 | 9/2008 | Imanishi et al. | |
| 7,696,345 B2 | 4/2010 | Prakash et al. | |
| 7,741,457 B2 | 6/2010 | Swayze et al. | |
| 7,875,733 B2 | 1/2011 | Bhat et al. | |
| 8,501,805 B2 | 8/2013 | Seth et al. | |
| 8,530,640 B2 | 9/2013 | Seth et al. | |
| 8,546,556 B2 | 10/2013 | Seth et al. | |
| 8,987,435 B2 * | 3/2015 | Swayze | C07H 21/00 536/23.1 |
| 8,993,738 B2 | 3/2015 | Prakash et al. | |
| 9,127,033 B2 * | 9/2015 | Prakash | C07H 19/067 |
| 9,156,873 B2 * | 10/2015 | Prakash | C07H 19/10 |
| 9,321,799 B2 * | 4/2016 | Prakash | C07H 19/067 |
| 9,976,138 B2 * | 5/2018 | Prakash | C12N 15/113 |
| 2004/0171570 A1 | 9/2004 | Allerson et al. | |
| 2005/0130923 A1 | 6/2005 | Bhat et al. | |
| 2007/0287831 A1 | 12/2007 | Seth et al. | |
| 2008/0039618 A1 | 2/2008 | Allerson et al. | |
| 2009/0253583 A1 | 10/2009 | Yoganathan | |
| 2010/0069472 A1 | 3/2010 | Hung et al. | |
| 2013/0059902 A1 | 3/2013 | Corey et al. | |

FOREIGN PATENT DOCUMENTS

| | | |
|---|---|---|
| WO | WO 2005/021570 | 3/2005 |
| WO | WO 2007/134181 | 11/2007 |
| WO | WO 2008/018795 | 2/2008 |
| WO | WO 2008/036406 | 3/2008 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/067647 | 5/2009 |
| WO | WO 2009/100320 | 8/2009 |
| WO | WO 2010/014592 | 2/2010 |
| WO | WO 2010/036698 | 4/2010 |
| WO | WO 2010/048549 | 4/2010 |
| WO | WO 2010/048585 | 4/2010 |
| WO | WO 2011/005860 | 1/2011 |
| WO | WO 2011/017521 | 2/2011 |
| WO | WO 2011/097388 | 8/2011 |
| WO | WO 2011/097614 | 8/2011 |
| WO | WO 2011/097641 | 8/2011 |
| WO | WO 2011/133871 | 10/2011 |
| WO | WO 2011/139695 | 11/2011 |
| WO | WO 2011/139699 | 11/2011 |
| WO | WO 2011/139702 | 11/2011 |
| WO | WO2012012443 A2 * | 1/2012 |
| WO | WO 2013/033223 | 3/2013 |
| WO | WO 2013/096679 | 6/2013 |

OTHER PUBLICATIONS

Hu et al. Chem Biol. 17:1183-1188 (Year: 2010).*
Yu et al. Cell 150: 895-908 (Year: 2012).*
Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.
Braasch et al., "Locked nucleic acid (LNA): fine-tuning the recognition of DNA and RNA" Chem. Biol. (2001) 8:1-7.
Brook et al., "Molecular basis of myotonic dystrophy: Expansion of a trinucleotide (CTG) repeat at the 3' end of a transcript encoding a protein kinase family member" Cell (1992) 68(4):799-808.
Cooper et al., "RNA and disease." Cell (2009) 136(4): 777-793.
Crooke et al., "Basic Principles of Antisense Therapeutics" Antisense Research and Application (1998) Chapter 1:1-50.
Crooke et al., "Pharmacokinetic Properties of Several Novel Oligonucleotide Analogs in mice" J. Pharmacol. Exp. Ther. (1996) 277: 923-937.

Davis et al., "Expansion of a CUG trinucleotide repeat in the 3' untranslated region of myotonic dystrophy protein kinase transcripts results in nuclear retention of transcripts" PNAS (1997) 94:7388-7393.
Elayadi et al., "Application of PNA and LNA oligomers to chemotherapy" Curr. Opinion Invens. Drugs (2001) 2: 558-561.
Englisch et al., "Chemically Modified Oligonucleotides as Probes and Inhibitors" Agnew Chem. Int. Ed. Engl. (1991) 30:613-629.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Hu et al. "Allele-Selective inhibition of mutant atrophin-1 expression by duplex & single-stranded RNAs" Biochemistry (2014) 53: 4510-4518.
Hu et al. "Allele-specific silencing of mutant huntingtin & ataxin-3 genes by targeting expanded CAG repeats in mRNAs" Nat. Biotech. (2009) 27: 478-484.
Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Krol et al., "Ribonuclease dicer cleaves triplet repeat hairpins into shorter repeats that silence specific targets" Molecular Cell (2007) 25:575-586.
Kroschwitz The Concise Encyclopedia of Polymer Science and Engineering, Kroschwitz, J.I., Ed., John Wiley & Sons, 1990, 858-859.
Kumar et al., "The first analogues of LNA (locked nucleic acids): phosphorothioate-LNA and 2'-thio-LNA" Bioorg Med Chem Lett. (1998) 8:2219-2222.
Letsinger et al., "Cholesteryl-conjugated oligonucleotides: Synthesis, properties, and activity as inhibitors of replication of human immunodeficiency virus in cell culture" PNAS (1989) 86:6553-6556.
Leumann, "DNA Analogues: From Supramolecular Principles to Biological Properties" Bioorg. & Med. Chem. (2002) 10:841-854.
Lin et al., "Neurological abnormalities in a knock-in mouse model of Huntington's disease" Human Molecular Genetics (2001) 10(2): 137-144.
Liu et al. "ss-siRNAs allele selectively inhibit ataxin-3 expression: multiple mechanisms for an alternative gene silencing strategy" Nuceic Acids Research (2013) 20: 9570-83.
Maher et al., "Comparative hybrid arrest by tandem antisense oligodeoxyribonucleotides or oligodeoxyribonucleoside methylphosphonates in a cell-free system" Nuc. Acid. Res. (1988) 16:341-3358.
Mankodi et al., "Expanding CUG Repeats Trigger Aberrant Splicing of ClC-1 Chloride Channel Pre-mRNA and Hyperexcitability of Skeletal Muscle in Myotonic Dystrophy" Mol. Cell. (2002) 10:35-44.
Manoharan et al., "Chemical Modifications to Improve Uptake and Bioavailability of Antisense Oligonucleotides" Ann N.Y. Acad. Sci. (1992) 660: 306-309.
Manoharan et al., "Introduction of a Lipophilic Thioether Tether in the Minor Groove of Nucleic Acids for Antisense Applications" Bioorg. Med. Chem. Lett. (1993) 3(12):2765-2770.
Manoharan et al., "Cholic Acid-Oligonucleotide Conjugates for Antisense Applications" Bioorg. Med. Chem. Lett. (1994) 4:1053-1060.
Manoharan et al., "Oligonucleotide Conjugates: Alteration of the Pharmacokinetic Properties of Antisense Agents" Nucleosides & Nucleotides (1995) 14(3-5):969-973.
Manoharan et al., "Lipidic Nucleic Acids" Tetrahedron Lett. (1995) 36(21):3651-3654.

(56) References Cited

OTHER PUBLICATIONS

Mishra et al., "Improved leishmanicidal effect of phosphorotioate antisense oligonucleotides by LDL-mediated delivery" Biochim. Biophys. Acta (1995) 1264:229-237.
O'Rourke et al., "Mechanisms of RNA-mediated Disease" J. Biol. Chem. (2009) 284(12): 7419-7423.
Oberhauser et al., "Effective incorporation of 2'-O-methyl-oligoribonucleotides into liposomes and enhanced cell association through modifications with thiocholesterol" Nucl. Acids Res. (1992) 20(3):533-538.
Orum et al., "Locked nucleic acids: A promising molecular family for gene-function analysis and antisense drug development" Curr. Opinion Mol. Ther. (2001) 3:239-243.
Prakash et al., "Antisense Oligonucleotides Containing Conformationally Constrained 2',4'-(N-Methoxy)aminomethylene and 2',40-Aminooxymethylene and 20-O,4'-C-Aminomethylene Bridged Nucleoside Analogues Show Improved Potency in Animal Models" J. Med. Chem. (2010) 53:1636-1650.
Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.
Sanghvi et al., "Eds.,Carbohydrate Modifications in Antisense Research" ACS Symposium Series 580; Chapters 3 and 4, 40-65.
Sanghvi et al., "Heterocyclic Base Modifications in Nucleic Acids & Their Applications in Antisense Oligonucleotides" Antisense Research and Applications Chapter 15, CRC Press, (1993) 273-288.
Shea et al., "Synthesis, hybridization properties and antiviral activity of lipid-oligodeoxynucleotide conjugates" Nucl. Acids Res. (1990) 18(13):3777-3783.
Singh et al., "LNA (locked nucleic acids): synthesis and high-affinity nucleic acid recognition" Chem. Commun. (1998) 455-456.
Singh et al., "Synthesis of 2'-amino-LNA: A novel conformationally restricted high-affinity oligonucleotide analogue with a handle" J. Org. Chem. (1998) 63: 10035-10039.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Svinarchuk et al., "Inhibition of HIV proliferation in MT-4 cells by antisense oligonucleotide conjugated to lipophilic groups" Biochimie (1993) 75:49-54.
Wahlestedt et al., "Potent and nontoxic antisense oligonucleotide containing locked nucleic acids" Proc. Natl. Acad. Sci. USA (2000) 97: 5633-5638.
Wheeler et al., "Reversal of RNA dominance by displacement of protein sequestered on triplet repeat RNA" Science (2009) 325:336-339.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
International Search Report for application PCT/US2012/052874 dated Nov. 28, 2012.
International Search Report for application PCT/US2014/049197 dated Feb. 4, 2015.
Hu, Jiaxin, Jing Liu, and David R. Corey. "Allele-selective inhibition of huntingtin expression by switching to an miRNA-like RNAi mechanism." *Chemistry& biology* 17.11 (2010): 1183-1188.
Yu, Dongbo, et al. "Single-stranded RNAs use RNAi to potently and allele-selectively inhibit mutant huntingtin expression." *Cell* 150.5 (2012): 895-908.

\* cited by examiner

A

B

SEQUENCE LISTING

```
<160> NUMBER OF SEQ ID NOS: 45

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
ggaaatatgg atgacagtgg                                              20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
atcctgagcc tctgatactc                                              20

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
gatgaggaag cagatctccg caggg                                        25

<210> SEQ ID NO 4
<211> LENGTH: 26
<212> TYPE: DNA
<213> ORGANISM: Artificial Sequence
```

```
<220> FEATURE:
<223> OTHER INFORMATION: Primer

<400> SEQUENCE: 4
aagacatggt cacagctgcc tgaagc                                            26

<210> SEQ ID NO 5
<211> LENGTH: 28
<212> TYPE: DNA
<213> ORGANISM: Artificial Sequence
<220> FEATURE:
<223> OTHER INFORMATION: Primer

<400> SEQUENCE: 5
gatttgcaga gggctctggc actaagtc                                          28

<210> SEQ ID NO 6
<211> LENGTH: 33
<212> TYPE: DNA
<213> ORGANISM: Artificial sequence
<220> FEATURE:
<223> OTHER INFORMATION: Primer

<400> SEQUENCE: 6
agcatgtctt cttcactcat agcatcactt ttc                                    33

<210> SEQ ID NO 7
<211> LENGTH: 21
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(21)
<223> OTHER INFORMATION: Bases at these positions are RNA

<400> SEQUENCE: 7
tcuacugcug cugcugcuga a                                                 21

<210> SEQ ID NO 8
<211> LENGTH: 21
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(21)
<223> OTHER INFORMATION: Bases at these positions are RNA

<400> SEQUENCE: 8
tcugaugcug cugcugcuga a                                                 21

<210> SEQ ID NO 9
<211> LENGTH: 21
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(21)
<223> OTHER INFORMATION: Bases at these positions are RNA

<400> SEQUENCE: 9
tcugcagcug cugcugcuga a                                                 21
```

```
<210> SEQ ID NO 10
<211> LENGTH: 21
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(21)
<223> OTHER INFORMATION: Bases at these positions are RNA

<400> SEQUENCE: 10
tcugcuacug cugcugcuga a                                      21

<210> SEQ ID NO 11
<211> LENGTH: 21
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(21)
<223> OTHER INFORMATION: Bases at these positions are RNA

<400> SEQUENCE: 11
tcugcugaug cugcugcuga a                                      21

<210> SEQ ID NO 12
<211> LENGTH: 21
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(21)
<223> OTHER INFORMATION: Bases at these positions are RNA

<400> SEQUENCE: 12
tcugcugcag cugcugcuga a                                      21

<210> SEQ ID NO 13
<211> LENGTH: 21
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(21)
<223> OTHER INFORMATION: Bases at these positions are RNA

<400> SEQUENCE: 13
tcugcugcua cugcugcuga a                                      21

<210> SEQ ID NO 14
<211> LENGTH: 21
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(21)
<223> OTHER INFORMATION: Bases at these positions are RNA

<400> SEQUENCE: 14
tcugcugcuu cugcugcuga a                                      21
```

<210> SEQ ID NO 15
<211> LENGTH: 21
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(21)
<223> OTHER INFORMATION: Bases at these positions are RNA

<400> SEQUENCE: 15
tcugcugcug augcugcuga a                                             21

<210> SEQ ID NO 16
<211> LENGTH: 21
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(21)
<223> OTHER INFORMATION: Bases at these positions are RNA

<400> SEQUENCE: 16
tcugcugcug cagcugcuga a                                             21

<210> SEQ ID NO 17
<211> LENGTH: 21
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(21)
<223> OTHER INFORMATION: Bases at these positions are RNA

<400> SEQUENCE: 17
tcugcugcug cuacugcuga a                                             21

<210> SEQ ID NO 18
<211> LENGTH: 21
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(21)
<223> OTHER INFORMATION: Bases at these positions are RNA

<400> SEQUENCE: 18
tcugcugcug cugcuacuga a                                             21

<210> SEQ ID NO 19
<211> LENGTH: 21
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(21)
<223> OTHER INFORMATION: Bases at these positions are RNA

<400> SEQUENCE: 19
tcugcugcaa cugcugcuga a                                               21

<210> SEQ ID NO 20
<211> LENGTH: 21
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(21)
<223> OTHER INFORMATION: Bases at these positions are RNA

<400> SEQUENCE: 20
tcugcugcaa augcugcuga a                                               21

<210> SEQ ID NO 21
<211> LENGTH: 21
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(21)
<223> OTHER INFORMATION: Bases at these positions are RNA

<400> SEQUENCE: 21
tcugcugaaa augcugcuga a                                               21

<210> SEQ ID NO 22
<211> LENGTH: 21
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(21)
<223> OTHER INFORMATION: Bases at these positions are RNA

<400> SEQUENCE: 22
tcuacugcua cugcuacuga a                                               21

<210> SEQ ID NO 23
<211> LENGTH: 21
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(21)
<223> OTHER INFORMATION: Bases at these positions are RNA

<400> SEQUENCE: 23
tcagcuguug cuacuguuga a                                               21

<210> SEQ ID NO 24
<211> LENGTH: 21
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(21)
<223> OTHER INFORMATION: Bases at these positions are RNA

<400> SEQUENCE: 24
tgcugcugcu gcugcugcua a    21

<210> SEQ ID NO 25
<211> LENGTH: 20
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(20)
<223> OTHER INFORMATION: Bases at these positions are RNA

<400> SEQUENCE: 25
tcugcugcag cugcugcuaa    20

<210> SEQ ID NO 26
<211> LENGTH: 19
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(19)
<223> OTHER INFORMATION: Bases at these positions are RNA

<400> SEQUENCE: 26
tcugcugcag cugcugcaa    19

<210> SEQ ID NO 27
<211> LENGTH: 18
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(18)
<223> OTHER INFORMATION: Bases at these positions are RNA

<400> SEQUENCE: 27
tcugcugcag cugcugaa    18

<210> SEQ ID NO 28
<211> LENGTH: 17
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(17)
<223> OTHER INFORMATION: Bases at these positions are RNA

<400> SEQUENCE: 28
tcugcugcag cugcuaa    17

<210> SEQ ID NO 29
<211> LENGTH: 16
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(16)
<223> OTHER INFORMATION: Bases at these positions are RNA

```
<400> SEQUENCE: 29
tcugcugcag cugcaa                                              16

<210> SEQ ID NO 30
<211> LENGTH: 15
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(15)
<223> OTHER INFORMATION: Bases at these positions are RNA

<400> SEQUENCE: 30
tcugcugcag cugaa                                               15

<210> SEQ ID NO 31
<211> LENGTH: 21
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(21)
<223> OTHER INFORMATION: Bases at these positions are RNA

<400> SEQUENCE: 31
tcugcugcag augcugcuga a                                        21

<210> SEQ ID NO 32
<211> LENGTH: 21
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(21)
<223> OTHER INFORMATION: Bases at these positions are RNA

<400> SEQUENCE: 32
tcugcugcag cagcugcuga a                                        21

<210> SEQ ID NO 33
<211> LENGTH: 21
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(21)
<223> OTHER INFORMATION: Bases at these positions are RNA

<400> SEQUENCE: 33
tcugcugcag cuacugcuga a                                        21

<210> SEQ ID NO 34
<211> LENGTH: 21
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(21)
<223> OTHER INFORMATION: Bases at these positions are RNA
```

```
<400> SEQUENCE: 34
tcugcugcag cugaugcuga a                                        21

<210> SEQ ID NO 35
<211> LENGTH: 21
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(21)
<223> OTHER INFORMATION: Bases at these positions are RNA

<400> SEQUENCE: 35
tcugcugcag cugcagcuga a                                        21

<210> SEQ ID NO 36
<211> LENGTH: 21
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(21)
<223> OTHER INFORMATION: Bases at these positions are RNA

<400> SEQUENCE: 36
tcugcugcag cugcuccuga a                                        21

<210> SEQ ID NO 37
<211> LENGTH: 21
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(21)
<223> OTHER INFORMATION: Bases at these positions are RNA

<400> SEQUENCE: 37
tcugcugcag cugcugauga a                                        21

<210> SEQ ID NO 38
<211> LENGTH: 21
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(21)
<223> OTHER INFORMATION: Bases at these positions are RNA

<400> SEQUENCE: 38
tcugcugcag cugcugcaga a                                        21

<210> SEQ ID NO 39
<211> LENGTH: 21
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(21)
```

<223> OTHER INFORMATION: Bases at these positions are RNA

<400> SEQUENCE: 39
tcugcugcag cugccgcuga a                                    21

<210> SEQ ID NO 40
<211> LENGTH: 21
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (2)..(21)
<223> OTHER INFORMATION: Bases at these positions are RNA

<400> SEQUENCE: 40
tcugcugcag cugcugccga a                                    21

<210> SEQ ID NO 41
<211> LENGTH: 19
<212> TYPE: RNA
<213> ORGANISM: Artificial sequence
<220> FEATURE:
<223> OTHER INFORMATION: Synthetic Oligonucleotide

<400> SEQUENCE: 41
gcugcugcug cugcugcug                                       19

<210> SEQ ID NO 42
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 42
gctgctgctg ctgctgctg                                       19

<210> SEQ ID NO 43
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 43
ctgctgctgc tgctgctgc                                       19

<210> SEQ ID NO 44
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 44
tgctgctgct gctgctgct                                       19

<210> SEQ ID NO 45
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 45
tgctgctgct gctgctggc                    19

METHODS AND COMPOUNDS USEFUL IN CONDITIONS RELATED TO REPEAT EXPANSION

STATEMENT AS TO FEDERALLY SPONSORED RESEARCH

This invention was made with government support under Grant Number GM073042 awarded by the National Institutes of Health. The government has certain rights in the invention.

SEQUENCE LISTING

The present application is being filed along with a Sequence Listing in electronic format. The Sequence Listing is provided as a file entitled CORE0118USASEQ_ST25.txt, created on Jan. 26, 2016, which is 12 Kb in size. The information in the electronic format of the sequence listing is incorporated herein by reference in its entirety.

BACKGROUND OF THE INVENTION

The present disclosure pertains generally to chemically-modified oligonucleotides for use in research, diagnostics, and/or therapeutics.

Certain RNA molecules are known to include repeat regions consisting essentially of repeating units of 3-5 nucleotides. Depending on the particular gene, the repeat region of a normal wild-type RNA molecule may comprise from about 5 up to about 11,000 copies of the repeating unit. In certain instances, the number of such repeating units can become increased and the resulting expanded repeat-containing RNA molecule may be disruptive to the cell. Certain diseases can result.

Certain oligonucleotides having nucleobase sequences complementary to a repeat region of a target RNA have been described, for example U.S. Patent Ser. No. 61/302,454; PCT International Application No. PCT/US2011/024019.

SUMMARY OF THE INVENTION

In certain embodiments, the present invention provides compounds and methods for modulating the expanded repeat-containing target nucleic acids. The present invention includes, but is not limited to the following numbered embodiments.

DETAILED DESCRIPTION

Figure 1:
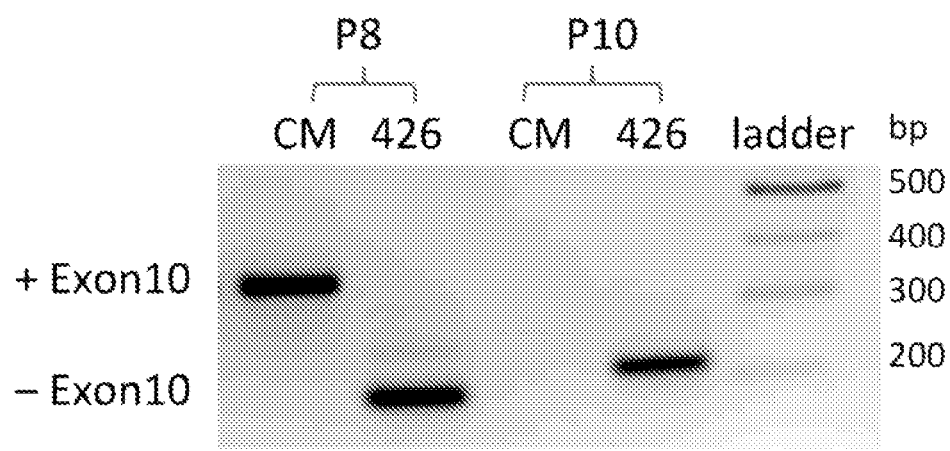
FIG. 1 shows the exclusion of exon 10 from ATXN3 mRNA induced by ss-siRNA compound ISIS No. 557426. Exon 10 includes the expanded CAG repeat associated with Spinocerebellar ataxia type 3.
Figure 2:
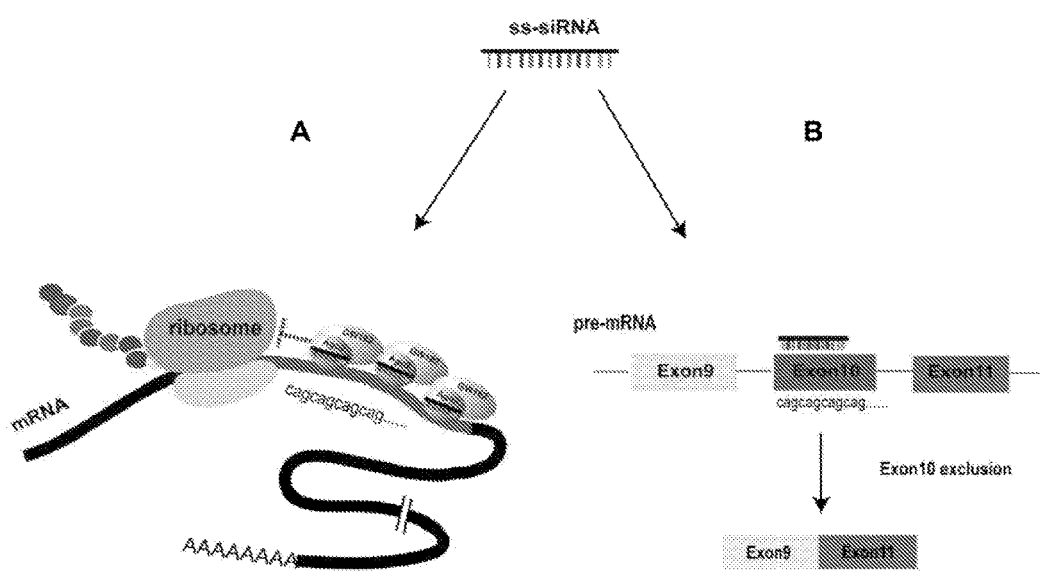
FIG. 2 is a schematic that shows ss-siRNA binding to the repeat region of exon 10 pre-mRNA and modulating splicing of the ATXN3 pre-mRNA to ATXN3 mRNA without exon 10.

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

A. Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., $21^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," $2^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. Chemical modifications of oligonucleotides include nucleoside modifications (including sugar moiety modifications and nucleobase modifications) and internucleoside linkage modifications. In reference to an oligonucleotide, chemical modification does not include differences only in nucleobase sequence.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety or a sugar surrogate.

As used herein, "substituted sugar moiety" means a furanosyl that is not a naturally occurring sugar moiety. Substituted sugar moieties include, but are not limited to furanosyls comprising substituents at the 2'-position, the 3'-position, the 5'-position and/or the 4'-position. Certain substituted sugar moieties are bicyclic sugar moieties.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —OCH$_2$CH$_2$OCH$_3$.

As used herein, "2'-F nucleoside" refers to a nucleoside comprising a sugar comprising fluorine at the 2' position. Unless otherwise indicated, the fluorine in a 2'-F nucleoside is in the ribo position (replacing the OH of a natural ribose).

As used herein, "2'-F ANA" refers to a 2'-F substituted nucleoside, wherein the fluoro group is in the arabino position.

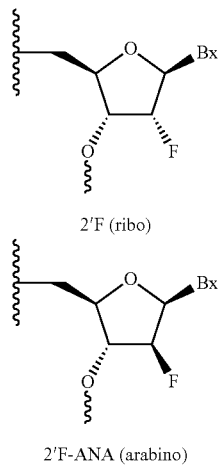

2'F (ribo)

2'F-ANA (arabino)

As used herein the term "sugar surrogate" means a structure that does not comprise a furanosyl and that is capable of replacing the naturally occurring sugar moiety of a nucleoside, such that the resulting nucleoside sub-units are capable of linking together and/or linking to other nucleosides to form an oligomeric compound which is capable of hybridizing to a complementary oligomeric compound. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH(CH$_3$)—O-2' bridge.

As used herein, "locked nucleic acid nucleoside" or "LNA" means a nucleoside comprising a bicyclic sugar moiety comprising a 4'-CH$_2$—O-2' bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "RNA-like nucleoside" means a modified nucleoside that adopts a northern configuration and functions like RNA when incorporated into an oligonucleotide. RNA-like nucleosides include, but are not limited to 2'-endo furanosyl nucleosides and RNA surrogates.

As used herein, "2'-endo-furanosyl nucleoside" means an RNA-like nucleoside that comprises a substituted sugar moiety that has a 2'-endo conformation. 2'-endo-furanosyl nucleosides include, but are not limited to: 2'-MOE, 2'-F, 2'-OMe, LNA, ENA, and cEt nucleosides.

As used herein, "RNA-surrogate nucleoside" means an RNA-like nucleoside that does not comprise a furanosyl. RNA-surrogate nucleosides include, but are not limited to hexitols and cyclopentanes.

As used herein, "phosphorous moiety" refers to a to monovalent $P^V$ phosphorus radical group. In certain embodiments, a phosphorus moiety is selected from: a phosphate, phosphonate, alkylphosphonate, aminoalkyl phosphonate, phosphorothioate, phosphoramidite, alkylphosphonothioate, phosphorodithioate, thiophosphoramidate, phosphotriester and the like. In certain embodiments, modified phosphorous moieties have the following structural formula:

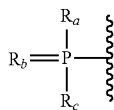

wherein:

$R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino; and $R_b$ is O or S.

The term "phosphate moiety" as used herein, refers to a terminal phosphate group that includes unmodified phosphates (—O—P(=O)(OH)OH) as well as modified phosphates. Modified phosphates include but are not limited to phosphates in which one or more of the O and OH groups is replaced with H, O, S, N(R) or alkyl where R is H, an amino protecting group or unsubstituted or substituted alkyl.

As used herein, "phosphate stabilizing modification" refers to a modification that results in stabilization of a 5'-phosphate moiety of the 5'-terminal nucleoside of an oligonucleotide, relative to the stability of an unmodified 5'-phosphate of an unmodified nucleoside under biologic conditions. Such stabilization of a 5'-phosphate group includes but is not limited to resistance to removal by phosphatases. Phosphate stabilizing modifications include, but are not limited to, modification of one or more of the atoms that binds directly to the phosphorus atom, modification of one or more atoms that link the phosphorus to the 5'-carbon of the nucleoside, and modifications at one or more other positions of the nucleoside that result in stabilization of the phosphate. In certain embodiments, a phosphate stabilizing modification comprises a carbon linking the phosphorous atom to the 5'-carbon of the sugar. Phosphate moieties that are stabilized by one or more phosphate stabilizing modification are referred to herein as "stabilized phosphate moieties."

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide. Oligomeric compounds also include naturally occurring nucleic acids.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "single-stranded" means an oligomeric compound that is not hybridized to its complement and which lacks sufficient self-complementarity to form a stable self-duplex.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid. In certain embodiments, antisense activity is a reduction of a gain-of-function of an expanded repeat-containing nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measurable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenylation, addition of 5'-cap), and translation.

As used herein, "target nucleic acid" means a nucleic acid molecule to which an antisense compound hybridizes.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, the term "expanded repeat-containing RNA" means a mutant RNA molecule having a nucleobase sequence that includes a repeat region consisting essentially of repeating units of 3-5 nucleobases that repeat at least 10 times in the repeating region, and wherein the presence or length of the repeat region affects the normal processing, function, or activity of the RNA or corresponding protein.

As used herein, the term "corresponding wild type RNA" means the non-mutant version of the expanded repeat-containing RNA having normal function and activity. Typically, corresponding wild type RNA molecules comprise a repeat region which is shorter than that of an expanded repeat-containing RNA.

As used herein, "selectivity" refers to the ability of an antisense compound to exert an antisense activity on a target nucleic acid to a greater extent than on a non-target nucleic acid.

As used herein, "mutant selective" refers to a compound that has a greater effect on a mutant nucleic acid than on the corresponding wild-type nucleic acid. In certain embodiments, the effect of a mutant selective compound on the mutant nucleic acid is 2, 3, 4, 5, 6, 7, 8, 9, 10, 15, 20, 25, 30, 35, 40, 50, 100 or more than 100 times greater than the effect of the mutant selective compound on the corresponding wild-type nucleic acid. In certain embodiments, such selectivity results from greater affinity of the mutant selective compound for the mutant nucleic acid than for the corresponding wild type nucleic acid. In certain embodiments, selectivity results from a difference in the structure of the mutant compared to the wild-type nucleic acid. In certain embodiments, selectivity results from differences in processing or sub-cellular distribution of the mutant and wild-type nucleic acids. In certain embodiments, some selectivity may be attributable to the presence of additional target sites in a mutant nucleic acid compared to the wild-type nucleic acid. For example, in certain embodiments, a target mutant allele comprises an expanded repeat region comprising more repeats than the wild-type allele. Thus, the wild-type allele has fewer sites available for hybridization of an antisense compound targeting the repeat region. In certain embodiments, a mutant selective compound has selectivity greater than the selectivity predicted by the increased number of target sites. In certain embodiments, the ratio of inhibition of a mutant allele to a wild type allele is equal to or greater than the ratio of the number of repeats in the mutant allele to the wild type allele. In certain embodiments, the ratio of inhibition of a mutant allele to a wild type allele is greater than the ratio of the number of repeats in the mutant allele to the wild type allele.

As used herein, "gain-of-function activity" means a biological activity attributed to an expanded repeat-containing RNA. For example, an expanded repeat-containing RNA may gain the ability to sequester ribonuclear proteins and impair the normal action of RNA processing in the nucleus (see Cooper, T. (2009) Cell 136, 777-793; O'Rourke, J R (2009) J. Biol. Chem. 284 (12), 7419-7423).

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "mismatch" means a nucleobase of a first oligomeric compound that is not capable of pairing with a nucleobase at a corresponding position of a second oligomeric compound, when the first and second oligomeric compound are aligned. Either or both of the first and second oligomeric compounds may be oligonucleotides.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, a fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "motif" means a pattern of chemical modifications in an oligonucleotide or a region thereof. Motifs may be defined by modifications at certain nucleosides and/or at certain linking groups of an oligonucleotide.

As used herein, "nucleoside motif" means a pattern of nucleoside modifications in an oligonucleotide or a region thereof. The linkages of such an oligonucleotide may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligonucleotide or a region thereof.

As used herein, "linkage motif" means a pattern of linkage modifications in an oligonucleotide or region thereof. The nucleosides of such an oligonucleotide may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleosides have "the same type of modification," even though the DNA nucleoside is unmodified. Such nucleosides having the same type modification may comprise different nucleobases.

As used herein, "separate regions" means portions of an oligonucleotide wherein the chemical modifications or the motif of chemical modifications of any neighboring portions include at least one difference to allow the separate regions to be distinguished from one another.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms that differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino(=$NR_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)N($R_{bb}$)($R_{cc}$)), thioureido (—N($R_{bb}$)C(S)N($R_{bb}$)—($R_{cc}$)), guanidinyl (—N($R_{bb}$)C(=$NR_{bb}$)N($R_{bb}$)($R_{cc}$)), amidinyl (—C(=$NR_{bb}$)N($R_{bb}$)($R_{cc}$) or —N($R_{bb}$)C(=$NR_{bb}$)($R_{aa}$)), thiol (—S$R_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S—(O)$_2$ $R_{bb}$). Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or polycyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein, "parenteral administration," means administration through injection or infusion. Parenteral administration includes, but is not limited to, subcutaneous administration, intravenous administration, or intramuscular administration.

As used herein, "systemic administration" means administration to an area other than the intended locus of activity. Examples or systemic administration are subcutaneous administration and intravenous administration, and intraperitoneal administration.

As used herein, "subcutaneous administration" means administration just below the skin.

As used herein, "intravenous administration" means administration into a vein.

As used herein, "cerebrospinal fluid" or "CSF" means the fluid filling the space around the brain and spinal cord.

As used herein, "administration into the cerebrospinal fluid" means any administration that delivers a substance directly into the CSF.

As used herein, "intracerebroventricular" or "ICV" mean administration into the ventricular system of the brain.

As used herein, "intrathecal" or "IT" means administration into the CSF under the arachnoid membrane which covers the brain and spinal cord. IT injection is performed through the theca of the spinal cord into the subarachnoid space, where a pharmaceutical agent is injected into the sheath surrounding the spinal cord.

B. Certain Compounds

In certain embodiments, the present invention provides compounds useful for studying, diagnosing, and/or treating a disease or disorder associated with an expanded repeat-containing RNA. In certain embodiments, compounds of the present invention comprise an oligonucleotide and a conjugate and/or terminal group. In certain embodiments, compounds consist of an oligonucleotide.

In certain embodiments, an oligonucleotide of the present invention has a nucleobase sequence comprising a region that is complementary to a repeat region of an expanded repeat-containing RNA. In certain embodiments, such oligonucleotides comprise one or more modifications.

a. Certain 5'-Terminal Nucleosides

In certain embodiments, compounds of the present invention comprise oligonucleotides comprising a stabilized phosphate moiety at the 5'-terminus. In certain such embodiments, the phosphorus atom of the stabilized phosphate moiety is attached to the 5'-terminal nucleoside through a phosphorus-carbon bond. In certain embodiments, the carbon of that phosphorus-carbon bond is in turn bound to the 5'-position of the nucleoside.

In certain embodiments, the oligonucleotide comprises a 5'-stabilized phosphate moiety having the following formula:

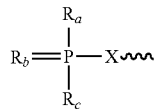

wherein:

$R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino;

$R_b$ is O or S;

X is substituted or unsubstituted C; and wherein X is attached to the 5'-terminal nucleoside. In certain embodiments, X is bound to an atom at the 5'-position of the 5'-terminal nucleoside. In certain such embodiments, the 5'-atom is a carbon and the bond between X and the 5'-carbon of the 5'-terminal nucleoside is a carbon-carbon single bond. In certain embodiments, it is a carbon-carbon double bond. In certain embodiments, it is a carbon-carbon triple bond. In certain embodiments, the 5'-carbon is substituted. In certain embodiments, X is substituted. In certain embodiments, X is unsubstituted.

In certain embodiments, the oligonucleotide comprises a 5'-stabilized phosphate moiety having the following formula:

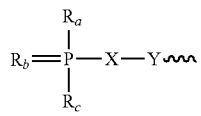

wherein:

$R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino;

$R_b$ is O or S;

X is substituted or unsubstituted C;

Y is selected from C, S, and N. In certain embodiments, Y is substituted or unsubstituted C. The bond between X and Y may be a single-, double-, or triple-bond.

In certain such embodiments, Y is the 5'-atom of the 5'-terminal nucleoside.

In certain embodiments, such oligonucleotides comprise a 5' terminal nucleoside having Formula I:

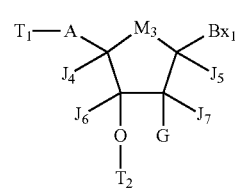

wherein:

$T_1$ is a phosphorus moiety;

$T_2$ is an internucleoside linking group linking the nucleoside of Formula I to the remainder of the oligonucleotide;

A has one of the formulas:

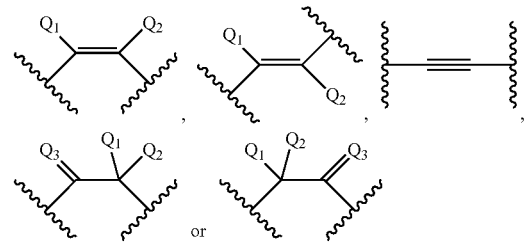

$Q_1$ and $Q_2$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy or $N(R_3)(R_4)$;

$Q_3$ is O, S, $N(R_5)$ or $C(R_6)(R_7)$;

each $R_3$, $R_4$ $R_5$, $R_6$ and $R_7$ is, independently, H, $C_1$-$C_6$ alkyl, substituted $C_1$-$C_6$ alkyl or $C_1$-$C_6$ alkoxy;

$M_3$ is O, S, $NR_{14}$, $C(R_{15})(R_{16})$, $C(R_{15})(R_{16})C(R_{17})(R_{18})$, $C(R_{15})=C(R_{17})$, $OC(R_{15})(R_{16})$ or $OC(R_{15})(Bx_2)$;

$R_{14}$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$R_{15}$, $R_{16}$, $R_{17}$ and $R_{18}$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

one of $Bx_1$ and $Bx_2$ is a nucleobase and the other of $Bx_1$ and $Bx_2$, if present, is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$J_4$, $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

or $J_4$ forms a bridge with either $J_5$ or $J_7$ wherein said bridge comprises from 1 to 3 linked biradical groups selected from O, S, $NR_{19}$, $C(R_{20})(R_{21})$, $C(R_{20})=C(R_{21})$, $C[=C(R_{20})(R_{21})]$ and $C(=O)$ and the other two of $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

each $R_{19}$, $R_{20}$ and $R_{21}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

G is H, OH, halogen or O—[C($R_8$)($R_9$)]$_n$—[(C=O)$_m$—$X_1$]$_j$—Z, or a conjugate group;

each $R_8$ and $R_9$ is, independently, H, halogen, $C_1$-$C_6$ alkyl or substituted $C_1$-$C_6$ alkyl;

$X_1$ is O, S or N($E_1$);

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or N($E_2$)($E_3$);

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, OC(=$X_2$)$J_1$, OC(=$X_2$)N($J_1$)($J_2$) and C(=$X_2$)N($J_1$)($J_2$);

$X_2$ is O, S or $NJ_3$;

each $J_1$, $J_2$ and $J_3$ is, independently, H or $C_1$-$C_6$ alkyl; and when j is 1 then Z is other than halogen or N($E_2$)($E_3$).

In certain embodiments, oligonucleotides comprise a 5'-terminal nucleoside having Formula II:

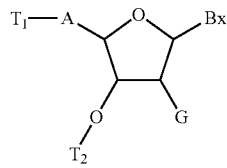

II wherein:

Bx is a nucleobase;

$T_1$ is an phosphorus moiety;

$T_2$ is an internucleoside linking group linking the compound of Formula II to the remainder of the oligonucleotide;

A has one of the formulas:

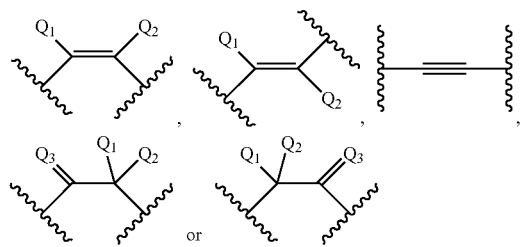

$Q_1$ and $Q_2$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy or N($R_3$)($R_4$);

$Q_3$ is O, S, N($R_5$) or C($R_6$)($R_7$);

each $R_3$, $R_4$ $R_5$, $R_6$ and $R_7$ is, independently, H, $C_1$-$C_6$ alkyl, substituted $C_1$-$C_6$ alkyl or $C_1$-$C_6$ alkoxy;

G is H, OH, halogen, O—[C($R_8$)($R_9$)]$_n$—[(C=O)$_m$—X]$_j$—Z or a conjugate group;

each $R_8$ and $R_9$ is, independently, H, halogen, $C_1$-$C_6$ alkyl or substituted $C_1$-$C_6$ alkyl;

X is O, S or N($E_1$);

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or N($E_2$)($E_3$);

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, OC(=L)$J_1$, OC(=L)N($J_1$)($J_2$) and C(=L)N($J_1$)($J_2$);

L is O, S or $NJ_3$;

each $J_1$, $J_2$ and $J_3$ is, independently, H or $C_1$-$C_6$ alkyl; and when j is 1 then Z is other than halogen or N($E_2$)($E_3$).

In certain embodiments, oligonucleotides comprise a 5'-terminal nucleoside having Formula III:

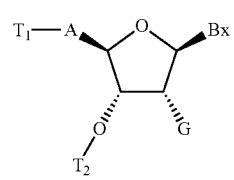

III wherein:

Bx is a nucleobase;

$T_1$ is a phosphorus moiety;

$T_2$ is an internucleoside linking group linking the compound of Formula III to the remainder of the oligonucleotide;

A has one of the formulas:

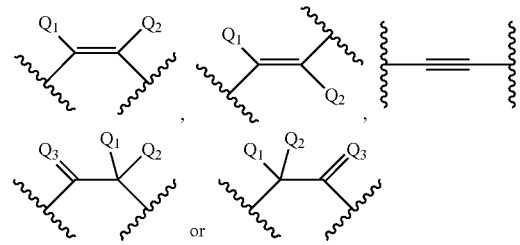

$Q_1$ and $Q_2$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy or N($R_3$)($R_4$);

$Q_3$ is O, S, N($R_5$) or C($R_6$)($R_7$);

each $R_3$, $R_4$ $R_5$, $R_6$ and $R_7$ is, independently, H, $C_1$-$C_6$ alkyl, substituted $C_1$-$C_6$ alkyl or $C_1$-$C_6$ alkoxy;

G is H, OH, halogen, O—[C($R_8$)($R_9$)]$_n$—[(C=O)$_m$—X]$_j$—Z, or a conjugate group;

each $R_8$ and $R_9$ is, independently, H, halogen, $C_1$-$C_6$ alkyl or substituted $C_1$-$C_6$ alkyl;

X is O, S or N($E_1$);

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or N($E_2$)($E_3$);

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=L)J_1$, $OC(=L)N(J_1)(J_2)$ and $C(=L)N(J_1)(J_2)$;

L is O, S or $NJ_3$;

each $J_1$, $J_2$ and $J_3$ is, independently, H or $C_1$-$C_6$ alkyl; and when j is 1 then Z is other than halogen or $N(E_2)(E_3)$.

In certain embodiments, oligonucleotides comprise a 5'-terminal nucleoside having Formula IV:

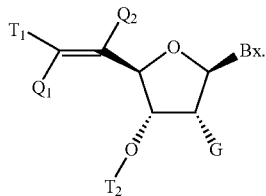

IV

In certain embodiments, oligonucleotide are provided comprising a compound having Formula IV wherein $Q_1$ and $Q_2$ are each H. In certain embodiments, oligonucleotide are provided comprising a compound having Formula IV wherein G is $O(CH_2)_2OCH_3$.

In certain embodiments, oligonucleotides comprise a 5'-terminal nucleoside having Formula V:

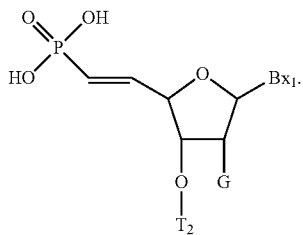

V

In certain embodiments, oligonucleotides comprise a nucleoside of Formula I, II, III, IV, or V. In certain such embodiments, the nucleoside of Formula I, II, III, IV, or V is at the 5'-terminus. In certain such embodiments, the remainder of the oligonucleotide comprises one or more modifications. Such modifications may include modified sugar moieties, modified nucleobases and/or modified internucleoside linkages. Certain such modifications which may be incorporated in an oligonucleotide comprising a nucleoside of Formula I, II, III, IV, or V at the 5'-terminus are known in the art.

b. Certain Sugar Moieties

In certain embodiments, compounds of the invention comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In certain embodiments, modified sugar moieties are substituted sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, 2'-$OCH_3$ ("OMe" or "O-methyl"), and 2'-$O(CH_2)_2OCH_3$ ("MOE"). In certain embodiments, sugar substituents at the 2' position is selected from allyl, amino, azido, thio, O-allyl, O—$C_1$-$C_{10}$ alkyl, O—$C_1$-$C_{10}$ substituted alkyl; $OCF_3$, $O(CH_2)_2SCH_3$, $O(CH_2)_2$—O—N(Rm)(Rn), and O—$CH_2$—C(=O)—N(Rm)(Rn), where each Rm and Rn is, independently, H or substituted or unsubstituted $C_1$-$C_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, SH, CN, OCN, $CF_3$, $OCF_3$, O, S, or $N(R_m)$-alkyl; O, S, or $N(R_m)$-alkenyl; O, S or $N(R_m)$-alkynyl; O-alkylenyl-O-alkyl, alkynyl, alkaryl, aralkyl, O-alkaryl, O-aralkyl, $O(CH_2)_2SCH_3$, O—$(CH_2)_2$—O—$N(R_m)(R_n)$ or O—$CH_2$—C(=O)—N$(R_m)(R_n)$, where each $R_m$ and $R_n$ is, independently, H, an amino protecting group or substituted or unsubstituted $C_1$-$C_{10}$ alkyl. These 2'-substituent groups can be further substituted with one or more substituent groups independently selected from hydroxyl, amino, alkoxy, carboxy, benzyl, phenyl, nitro ($NO_2$), thiol, thioalkoxy (S-alkyl), halogen, alkyl, aryl, alkenyl and alkynyl.

In certain embodiments, a 2'-substituted nucleoside comprises a 2'-substituent group selected from F, $NH_2$, $N_3$, $OCF_3$, O—$CH_3$, $O(CH_2)_3NH_2$, $CH_2$—CH=$CH_2$, O—$CH_2$—CH=$CH_2$, $OCH_2CH_2OCH_3$, $O(CH_2)_2SCH_3$, O—$(CH_2)_2$—O—$N(R_m)(R_n)$, $O(CH_2)_2O(CH_2)_2N(CH_3)_2$, and N-substituted acetamide (O—$CH_2$—C(=O)—$N(R_m)$($R_n$) where each $R_m$ and $R_n$ is, independently, H, an amino protecting group or substituted or unsubstituted $C_1$-$C_{10}$ alkyl.

In certain embodiments, a 2'-substituted nucleoside comprises a sugar moiety comprising a 2'-substituent group selected from F, $OCF_3$, O—$CH_3$, $OCH_2CH_2OCH_3$, $O(CH_2)_2$ $SCH_3$, O—$(CH_2)_2$—O—$N(CH_3)_2$, —$O(CH_2)_2O$ $(CH_2)_2N(CH_3)_2$, and O—$CH_2$—C(=O)—N(H)$CH_3$.

In certain embodiments, a 2'-substituted nucleoside comprises a sugar moiety comprising a 2'-substituent group selected from F, O—$CH_3$, and $OCH_2CH_2OCH_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C($R_a$) ($R_b$)]$_n$—, —[C($R_a$)($R_b$)]$_n$—O—, —C($R_aR_b$)—N(R)—O— or, —C($R_aR_b$)—O—N(R)—; 4'-$(CH_2)_2$-2', 4'-$(CH_2)$—O-2' (LNA); 4'-$(CH_2)$—S-2; 4'-$(CH_2)_2$—O-2' (ENA); 4'-CH ($CH_3$)—O-2' (cEt) and 4'-CH($CH_2OCH_3$)—O-2', and analogs thereof (see, e.g., U.S. Pat. No. 7,399,845, issued on Jul. 15, 2008); 4'-C($CH_3$)($CH_3$)—O-2' and analogs thereof, (see, e.g., WO2009/006478, published Jan. 8, 2009); 4'-CH₂—N(OCH₃)-2' and analogs thereof (see, e.g., WO2008/150729, published Dec. 11, 2008); 4'-CH₂—O—N(CH₃)-2' (see, e.g., US2004/0171570, published Sep. 2, 2004); 4'-CH₂—O—N(R)-2', and 4'-CH₂—N(R)—O-2'-, wherein each R is, independently, H, a protecting group, or $C_1$-$C_{12}$ alkyl; 4'-CH₂—N(R)—O-2', wherein R is H, $C_1$-$C_{12}$ alkyl, or a protecting group (see, U.S. Pat. No. 7,427,672, issued on Sep. 23, 2008); 4'-CH₂—C(H)(CH₃)-2' (see, e.g., Chattopadhyaya, et al., *J. Org. Chem.*, 2009, 74, 118-134); and 4'-CH₂—C(=CH₂)-2' and analogs thereof (see, published PCT International Application WO 2008/154401, published on Dec. 8, 2008).

In certain embodiments, such 4' to 2' bridges independently comprise from 1 to 4 linked groups independently selected from —[C($R_a$)($R_b$)]$_n$—, —C($R_a$)=C($R_b$)—, —C($R_a$)=N—, —C(=N$R_a$)—, —C(=O)—, —C(=S)—, —O—, —Si($R_a$)₂—, —S(=O)$_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)₂-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-CH₂—O-2') BNA, (B) β-D-Methyleneoxy (4'-CH₂—O-2') BNA (also referred to as locked nucleic acid or LNA), (C) Ethyleneoxy (4'-(CH₂)₂—O-2') BNA, (D) Aminooxy (4'-CH₂—O—N(R)-2') BNA, (E) Oxyamino (4'-CH₂—N(R)—O-2') BNA, (F) Methyl(methyleneoxy) (4'-CH(CH₃)—O-2') BNA (also referred to as constrained ethyl or cEt), (G) methylene-thio (4'-CH₂—S-2') BNA, (H) methylene-amino (4'-CH2-N(R)-2') BNA, (I) methyl carbocyclic (4'-CH₂—CH(CH₃)-2') BNA, (J) propylene carbocyclic (4'-(CH₂)₃-2') BNA, and (K) Methoxy(ethyleneoxy) (4'-CH(CH₂OMe)-O-2') BNA (also referred to as constrained MOE or cMOE) as depicted below.

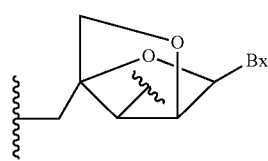
(A)

-continued

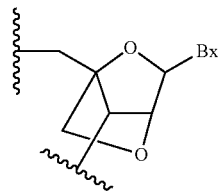
(B)

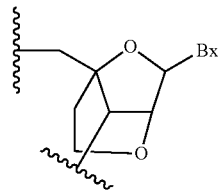
(C)

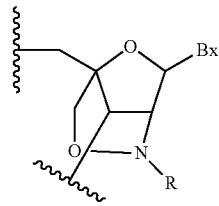
(D)

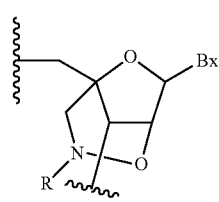
(E)

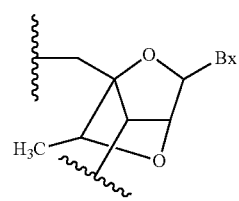
(F)

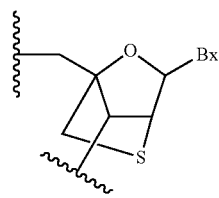
(G)

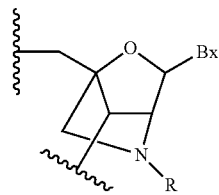
(H)

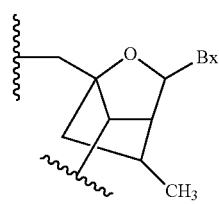
(I)

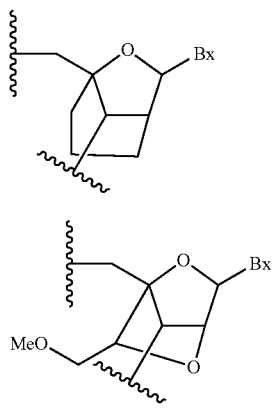

(J)

(K)

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et al., *Curr. Opinion Invens. Drugs*, 2001, 2, 5561; Braasch et al., *Chem. Biol.*, 2001, 8, 1-7; Orum et al., *Curr. Opinion Mol. Ther.*, 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') bicyclic nucleosides have been incorporated into antisense oligonucleotides that showed antisense activity (Frieden et al., *Nucleic Acids Research*, 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfur, carbon or nitrogen atom. In certain such embodiments, such modified sugar moiety also comprises bridging and/or non-bridging substituents as described above. For example, certain sugar surrogates comprise a 4'-sulfur atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research*, 1997, 25(22), 4429-4443 and Albaek et al., *J. Org. Chem.*, 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), annitol nucleic acid (ANA), mannitol nucleic acid (MNA) (see Leumann, C J. *Bioorg. & Med. Chem.* (2002) 10:841-854), fluoro HNA (F-HNA), and those compounds having Formula VII:

VII

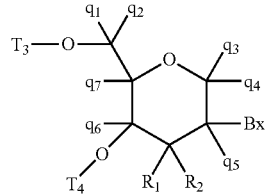

wherein independently for each of said at least one tetrahydropyran nucleoside analog of Formula VII:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from hydrogen, halogen, substituted or unsubstituted alkoxy, $NJ_1J_2$, $SJ_1$, $N_3$, OC(=X)$J_1$, OC(=X)$NJ_1J_2$, $NJ_3$C(=X)$NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclo and tricyclo sugar surrogate ring systems are also known in the art that can be used to modify nucleosides for incorporation into antisense compounds (see, e.g., review article: Leumann, J C, *Bioorganic & Medicinal Chemistry*, 2002, 10, 841-854).

Combinations of modifications are also provided without limitation, such as 2'-F-5'-methyl substituted nucleosides (see PCT International Application WO 2008/101157 Published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., J. Am. Chem. Soc. 2007, 129(26), 8362-8379).

In certain embodiments, the present invention provides oligonucleotides comprising modified nucleosides. Those modified nucleotides may include modified sugars, modified nucleobases, and/or modified linkages. The specific modifications are selected such that the resulting oligonucleotides possess desirable characteristics. In certain embodiments, oligonucleotides comprise one or more RNA-like nucleosides. In certain embodiments, oligonucleotides comprise one or more DNA-like nucleotides.

c. Certain Nucleobases

In certain embodiments, nucleosides of the present invention comprise one or more unmodified nucleobases. In certain embodiments, nucleosides of the present invention comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine ([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459, 255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

d. Certain Internucleoside Linkages

In certain embodiments, the present invention provides oligonucleotides comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Modified linkages, compared to natural phosphodiester linkages, can be used to alter, typically increase, nuclease resistance of the oligonucleotide. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

e. Certain Motifs

In certain embodiments, the present invention provides compounds comprising oligonucleotides. In certain embodiments, such oligonucleotides comprise one or more chemical modification. In certain embodiments, chemically modified oligonucleotides comprise one or more modified sugars. In certain embodiments, chemically modified oligonucleotides comprise one or more modified nucleobases. In certain embodiments, chemically modified oligonucleotides comprise one or more modified internucleoside linkages. In certain embodiments, the chemical modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

i. Certain Sugar Motifs

In certain embodiments, oligonucleotides comprise one or more type of modified sugar moieties and/or naturally occurring sugar moieties arranged along an oligonucleotide or region thereof in a defined pattern or sugar modification motif Such motifs may include any of the sugar modifications discussed herein and/or other known sugar modifications.

In certain embodiments, the oligonucleotides comprise or consist of a region having uniform sugar modifications. In certain such embodiments, each nucleoside of the region comprises the same RNA-like sugar modification. In certain embodiments, each nucleoside of the region is a 2'-F nucleoside. In certain embodiments, each nucleoside of the region is a 2'-OMe nucleoside. In certain embodiments, each nucleoside of the region is a 2'-MOE nucleoside. In certain embodiments, each nucleoside of the region is a cEt nucleoside. In certain embodiments, each nucleoside of the region is an LNA nucleoside. In certain embodiments, the uniform region constitutes all or essentially all of the oligonucleotide. In certain embodiments, the region constitutes the entire oligonucleotide except for 1-4 terminal nucleosides.

In certain embodiments, oligonucleotides of the present invention comprise one or more regions of alternating sugar modifications, wherein the nucleosides alternate between nucleosides having a sugar modification of a first type and nucleosides having a sugar modification of a second type. In certain embodiments, nucleosides of both types are RNA-like nucleosides. In certain embodiments the alternating nucleosides are selected from: 2'-Ome, 2'-F, 2'-MOE, LNA, and cEt. In certain embodiments, the alternating modifications are 2'-F and 2'-Ome. Such regions may be contiguous or may be interrupted by differently modified nucleosides or conjugated nucleosides.

In certain embodiments, the alternating region of alternating modifications each consist of a single nucleoside (i.e., the pattern is $(AB)_xA_y$ wherein A is a nucleoside having a sugar modification of a first type and B is a nucleoside having a sugar modification of a second type; x is 1-20 and y is 0 or 1). In certain embodiments, one or more alternating regions in an alternating motif includes more than a single nucleoside of a type. For example, oligonucleotides of the present invention may include one or more regions of any of the following nucleoside motifs:

AABBAA;
ABBABB;
AABAAB;
ABBABAABB;
ABABAA;
AABABAB;
ABABAA;
ABBAABBABABAA;
BABBAABBABABAA; or
ABABBAABBABABAA;

wherein A is a nucleoside of a first type and B is a nucleoside of a second type. In certain embodiments, A and B are each selected from 2'-F, 2'-Ome, BNA, and MOE.

In certain embodiments, oligonucleotides having such an alternating motif also comprise a 5' terminal nucleoside of Formula I, II, III, IV, or V.

In certain embodiments, oligonucleotides of the present invention comprise a region having a 2-2-3 motif Such regions comprises the following motif:

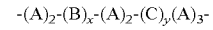

wherein: A is a first type of modified nucleoside;
B and C, are nucleosides that are differently modified than A, however, B and C may have the same or different modifications as one another;
x and y are from 1 to 15.

In certain embodiments, A is a 2'-Ome modified nucleoside. In certain embodiments, B and C are both 2'-F modified nucleosides. In certain embodiments, A is a 2'-Ome modified nucleoside and B and C are both 2'-F modified nucleosides.

It is to be understood, that certain of the above described motifs and modifications may be combined. Since a motif may comprise only a few nucleosides, a particular oligonucleotide may comprise two or more motifs. By way of non-limiting example, in certain embodiments, oligonucleotides may have nucleoside motifs as described in the table below. In the table below, the term "None" indicates that a particular feature is not present in the oligonucleotide. For example, "None" in the column labeled "5' motif/modification" indicates that the 5' end of the oligonucleotide comprises the first nucleoside of the central motif

| 5' motif/modification | Central Motif | 3'-motif |
|---|---|---|
| Compound of Formula I, II, III, IV, or V | Alternating | 2 MOE nucleosides |
| Compound of Formula I, II, III, IV, or V | 2-2-3 motif | 2 MOE nucleosides |
| Compound of Formula I, II, III, IV, or V | Uniform | 2 MOE nucleosides |
| Compound of Formula I, II, III, IV, or V | Alternating | 2 MOE nucleosides |
| Compound of Formula I, II, III, IV, or V | Alternating | 2 MOE A's |
| Compound of Formula I, II, III, IV, or V | 2-2-3 motif | 2 MOE A's |
| Compound of Formula I, II, III, IV, or V | Uniform | 2 MOE A's |
| Compound of Formula I, II, III, IV, or V | Alternating | 2 MOE U's |
| Compound of Formula I, II, III, IV, or V | 2-2-3 motif | 2 MOE U's |
| Compound of Formula I, II, III, IV, or V | Uniform | 2 MOE U's |
| Compound of Formula I, II, III, IV, or V | Alternating | 2 MOE nucleosides |
| Compound of Formula I, II, III, IV, or V | 2-2-3 motif | 2 MOE nucleosides |
| Compound of Formula I, II, III, IV, or V | Uniform | 2 MOE nucleosides |

In certain embodiments, oligonucleosides have the following sugar motif:

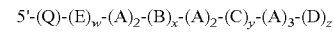

wherein:
Q is a nucleoside comprising a stabilized phosphate moiety. In certain embodiments, Q is a nucleoside having Formula I, II, III, IV, or V;
A is a first type of modified nucleoside;
B, C, D, and E are nucleosides that are differently modified than A, however, B, C, D, and E may have the same or different modifications as one another;
w and z are from 0 to 15;
x and y are from 1 to 15.

In certain embodiments, the sum of w, x, and y is 5-25.

In certain embodiments, oligonucleotides have the following sugar motif:

wherein:

Q is a nucleoside comprising a stabilized phosphate moiety. In certain embodiments, Q is a nucleoside having Formula I, II, III, IV, or V;

A is a first type of modified nucleoside;

B is a second type of modified nucleoside;

D is a modified nucleoside comprising a modification different from the nucleoside adjacent to it. Thus, if y is 0, then D must be differently modified than B and if y is 1, then D must be differently modified than A. In certain embodiments, D differs from both A and B.

X is 5-15;
Y is 0 or 1;
Z is 0-4.

In certain embodiments, oligonucleosides have the following sugar motif:

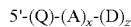

wherein:

Q is a nucleoside comprising a stabilized phosphate moiety. In certain embodiments, Q is a nucleoside having Formula I, II, III, IV, or V;

A is a first type of modified nucleoside;

D is a modified nucleoside comprising a modification different from A.

X is 11-30;
Z is 0-4.

In certain embodiments A, B, C, and D in the above motifs are selected from: 2'-Ome, 2'-F, 2'-MOE, LNA, and cEt. In certain embodiments, D represents terminal nucleosides. In certain embodiments, such terminal nucleosides are not designed to hybridize to the target nucleic acid (though one or more might hybridize by chance). In certain embodiments, the nucleobase of each D nucleoside is adenine, regardless of the identity of the nucleobase at the corresponding position of the target nucleic acid. In certain embodiments the nucleobase of each D nucleoside is thymine.

ii. Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate internucleoside linkages. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least one block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Oligonucleotides having any of the various sugar motifs described herein, may have any linkage motif. For example, the oligonucleotides, including but not limited to those described above, may have a linkage motif selected from non-limiting the table below:

| 5' most linkage | Central region | 3'-region |
|---|---|---|
| PS | Alternating PO/PS | 6 PS |
| PS | Alternating PO/PS | 7 PS |
| PS | Alternating PO/PS | 8 PS | iii. Certain Nucleobase Modification Motifs

In certain embodiments, oligonucleotides comprise chemical modifications to nucleobases arranged along the oligonucleotide or region thereof in a defined pattern or nucleobases modification motif. In certain such embodiments, nucleobase modifications are arranged in a gapped motif. In certain embodiments, nucleobase modifications are arranged in an alternating motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

a. Certain Overall Lengths

In certain embodiments, the present invention provides oligonucleotides of any of a variety of ranges of lengths. In certain embodiments, the invention provides oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the invention provides oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligonucleotide of a compound is limited, whether to a range or to a specific number, the compound may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range.

b. Certain Oligonucleotides

In certain embodiments, oligonucleotides of the present invention are characterized by their sugar motif, internucleoside linkage motif, nucleobase modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. Thus, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. One of skill in the art will appreciate that such motifs may be combined to create a variety of oligonucleotides, such as those provided in the non-limiting table below. As is apparent from the above, non-limiting tables, the lengths of the regions defined by a nucleoside motif and that of a linkage motif need not be the same. To further illustrate, and not to limit in any way, nucleoside motifs and sequence motifs are combined to show five non-limiting examples in the table below. The first column of the table lists nucleosides and linkages by position from N1 (the first nucleoside at the 5'-end) to N20 (the $20^{th}$ position from the 5'-end). In certain embodiments, oligonucleotides of the present invention are longer than 20 nucleosides (the table is merely exemplary). Certain positions in the table recite the nucleoside or linkage "none" indicating that the oligonucleotide has no nucleoside at that position.

| Pos | A | B | C | D | E |
|---|---|---|---|---|---|
| N1 | Formula I, II, III, IV, or V | Formula I, II, III, IV, or V | Formula I, II, III, IV, or V | Formula I, II, III, IV, or V | Formula I, II, III, IV, or V |
| L1 | PS | PS | PS | PS | PO |
| N2 | 2'-F | 2'-F | 2'-F | 2'-Ome | MOE |
| L2 | PS | PS | PS | PO | PS |
| N3 | 2'-Ome | 2'-F | 2'-F | 2'-F | 2'-F |
| L3 | PO | PS | PS | PS | PS |
| N4 | 2'-F | 2'-F | 2'-F | 2'-Ome | 2'-F |
| L4 | PS | PS | PS | PO | PS |
| N5 | 2'-Ome | 2'-F | 2'-F | 2'-F | 2'-Ome |
| L5 | PO | PS | PS | PS | PO |
| N6 | 2'-F | 2'-Ome | 2'-F | 2'-Ome | 2'-Ome |
| L6 | PS | PO | PS | PO | PO |
| N7 | 2'-Ome | 2'-Ome | 2'-F | 2'-F | 2'-Ome |
| L7 | PO | PO | PS | PS | PO |
| N8 | 2'-F | 2'-F | 2'-F | 2'-Ome | 2'-F |
| L8 | PS | PS | PS | PO | PS |
| N9 | 2'-Ome | 2'-F | 2'-F | 2'-F | 2'-F |
| L9 | PO | PS | PS | PS | PS |
| N10 | 2'-F | 2'-Ome | 2'-F | 2'-Ome | 2'-Ome |
| L10 | PS | PO | PS | PO | PO |
| N11 | 2'-Ome | 2'-Ome | 2'-F | 2'-F | 2'Ome |
| L11 | PO | PO | PS | PS | PO |
| N12 | 2'-F | 2'-F | 2'-F | 2'-F | 2'-F |
| L12 | PS | PS | PS | PO | PS |
| N13 | 2'-Ome | 2'-F | 2'-F | 2'-F | 2'-F |
| L13 | PO | PS | PS | PS | PS |
| N14 | 2'-F | 2'-Ome | 2'-F | 2'-F | 2'-F |
| L14 | PS | PS | PS | PS | PS |
| N15 | 2'-Ome | 2'Ome | 2'-F | 2'-F | 2'-MOE |
| L15 | PS | PS | PS | PS | PS |
| N16 | 2'-F | 2'Ome | 2'-F | 2'-F | 2'-MOE |
| L16 | PS | PS | PS | PS | PS |
| N17 | 2'-Ome | 2'-MOE U | 2'-F | 2'-F | 2'-MOE |
| L17 | PS | PS | PS | PS | None |
| N18 | 2'-F | 2'-MOE U | 2'-F | 2'-Ome | None |
| L18 | PS | None | PS | PS | None |
| N19 | 2'-MOE U | None | 2'-MOE U | 2'-MOE A | None |
| L19 | PS | None | PS | PS | None |
| N20 | 2'-MOE U | None | 2'-MOE U | 2'-MOE A | None |

In the above, non-limiting examples:

Column A represent an oligonucleotide consisting of 20 linked nucleosides, wherein the oligonucleotide comprises: a modified 5'-terminal nucleoside of Formula I, II, III, IV, or V; a region of alternating nucleosides; a region of alternating linkages; two 3'-terminal MOE nucleosides, each of which comprises a uracil base; and a region of six phosphorothioate linkages at the 3'-end.

Column B represents an oligonucleotide consisting of 18 linked nucleosides, wherein the oligonucleotide comprises: a modified 5'-terminal nucleoside of Formula I, II, III, IV, or V; a 2-2-3 motif wherein the modified nucleoside of the 2-2-3 motif are 2'O-Me and the remaining nucleosides are all 2'-F; two 3'-terminal MOE nucleosides, each of which comprises a uracil base; and a region of six phosphorothioate linkages at the 3'-end.

Column C represents an oligonucleotide consisting of 20 linked nucleosides, wherein the oligonucleotide comprises: a modified 5'-terminal nucleoside of Formula I, II, III, IV, or V; a region of uniformly modified 2'-F nucleosides; two 3'-terminal MOE nucleosides, each of which comprises a uracil base; and wherein each internucleoside linkage is a phosphorothioate linkage.

Column D represents an oligonucleotide consisting of 20 linked nucleosides, wherein the oligonucleotide comprises: a modified 5'-terminal nucleoside of Formula I, II, III, IV, or V; a region of alternating 2'-Ome/2'-F nucleosides; a region of uniform 2'F nucleosides; a region of alternating phosphorothioate/phosphodiester linkages; two 3'-terminal MOE nucleosides, each of which comprises an adenine base; and a region of six phosphorothioate linkages at the 3'-end.

Column E represents an oligonucleotide consisting of 17 linked nucleosides, wherein the oligonucleotide comprises: a modified 5'-terminal nucleoside of Formula I, II, III, IV, or V; a 2-2-3 motif wherein the modified nucleoside of the 2-2-3 motif are 2'F and the remaining nucleosides are all 2'-Ome; three 3'-terminal MOE nucleosides.

The above examples are provided solely to illustrate how the described motifs may be used in combination and are not intended to limit the invention to the particular combinations or the particular modifications used in illustrating the combinations. Further, specific examples herein, including, but not limited to those in the above table are intended to encompass more generic embodiments. For example, column A in the above table exemplifies a region of alternating 2'-Ome and 2'-F nucleosides. Thus, that same disclosure also exemplifies a region of alternating different 2'-modifications. It also exemplifies a region of alternating 2'-O-alkyl and 2'-halogen nucleosides. It also exemplifies a region of alternating differently modified nucleosides. All of the examples throughout this specification contemplate such generic interpretation.

It is also noted that the lengths of the oligonucleotides, such as those exemplified in the above tables, can be easily manipulated by lengthening or shortening one or more of the described regions, without disrupting the motif.

In certain embodiments, the invention provides oligonucleotides wherein the 5'-terminal nucleoside (position 1) is a compound of Formula I, II, III, IV, or V and the position 2 nucleoside comprises a 2'-modification. In certain such embodiments, the 2'-modification of the position 2 nucleoside is selected from halogen, alkyl, and substituted alkyl. In certain embodiments, the 2'-modification of the position 2 nucleoside is selected from 2'-F and 2'-alkyl. In certain embodiments, the 2'-modification of the position 2 nucleoside is 2'-F. In certain embodiments, the 2'-substituted of the position 2 nucleoside is an unmodified OH (as in naturally occurring RNA).

In certain embodiments, the position 3 nucleoside is a modified nucleoside. In certain embodiments, the position 3 nucleoside is a bicyclic nucleoside. In certain embodiments, the position 3 nucleoside comprises a sugar surrogate. In certain such embodiments, the sugar surrogate is a tetrahydropyran. In certain embodiments, the sugar of the position 3 nucleoside is a F-HNA.

In certain embodiments, an antisense compound comprises an oligonucleotide comprising 10 to 30 linked nucleosides wherein the oligonucleotide comprises: a position 1 modified nucleoside of Formula I, II, III, IV, or V; a position 2 nucleoside comprising a sugar moiety which is differently modified compared to the sugar moiety of the position 1 modified nucleoside; and from 1 to 4 3'-terminal group nucleosides each comprising a 2'-modification; and wherein at least the seven 3'-most internucleoside linkages are phosphorothioate linkages.

c. Certain Conjugate Groups

In certain embodiments, oligonucleotides are modified by attachment of one or more conjugate groups. In general, conjugate groups modify one or more properties of the attached oligonucleotide, including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligonucleotide. Conjugate groups include without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylaminocarbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

In certain embodiments, conjugate groups are directly attached to oligonucleotides. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligonucleotide. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide. In certain embodiments, conjugate groups are near the 3'-end. In certain embodiments, conjugates are attached at the 3' end of an oligonucleotide, but before one or more terminal group nucleosides. In certain embodiments, conjugate groups are placed within a terminal group. In certain embodiments, a conjugate group is attached to the 3'-terminal nucleoside. In certain such embodiment, it is attached at the 3'-position of the 3'-terminal nucleoside. In certain embodiments, it is attached at the 2'-position of the 3'-terminal nucleoside.

In certain embodiments, compounds comprise an oligonucleotide. In certain embodiments, an compound comprises an oligonucleotide and one or more conjugate and/or terminal groups. Such conjugate and/or terminal groups may be added to oligonucleotides having any of the chemical motifs discussed above. Thus, for example, a compound comprising an oligonucleotide having region of alternating nucleosides may comprise a terminal group.

In certain embodiments, a conjugate is attached at the 2'-position of a nucleoside. In certain embodiments, a conjugate is attached to a nucleoside at one or more of: position 1, 6 or 8 of the oligonucleotide, counting from the 5'-end. In certain embodiments a conjugate is attached to a nucleoside at one or more of: position 13, 15, or 20 of the oligonucleotide, counting from the 3'-end.

In certain embodiments, conjugates interrupt motifs. For example, in certain embodiments, oligonucleotides of the present invention have an alternating motif that spans positions 1-19 and a conjugate at position 8 (from the 5'-end) as follows:

Po-ABABABAXABABABABABA-

Wherein A represents nucleosides of a first-type;

B represents nucleosides of a second type; and

X represents a nucleoside to which a conjugate is attached.

In certain embodiments, A and B are 2'-modifications and X is a conjugate attached at the 2'-position. Thus, the motif of alternating 2'-modifications is interrupted by the conjugate. Such an oligonucleotide may, nevertheless be described as having an alternating motif.

d. Antisense Compounds

In certain embodiments, compounds of the present invention are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid or reduce non-specific hybridization to non-target nucleic acid sequences under conditions in which specific hybridization is desired (e.g., under physiological conditions for in vivo or therapeutic uses, and under conditions in which assays are performed in the case of in vitro assays). In certain embodiments, oligonucleotides are selective between a target and non-target, even though both target and non-target comprise the target sequence. In such embodiments, selectivity may result from relative accessability of the target region of one nucleic acid molecule compared to the other.

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, oligonucleotides are 90% complementary to the target nucleic acid.

In certain embodiments, oligonucleotides are 85% complementary to the target nucleic acid. In certain embodiments, oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

In certain embodiments, oligonucleotides comprise a hybridizing region and a terminal region. In certain such embodiments, the hybridizing region consists of 12-30 linked nucleosides and is fully complementary to the target nucleic acid. In certain embodiments, the hybridizing region includes one mismatch relative to the target nucleic acid. In certain embodiments, the hybridizing region includes two mismatches relative to the target nucleic acid. In certain embodiments, the hybridizing region includes three mismatches relative to the target nucleic acid. In certain embodiments, the hybridizing region includes four mismatches relative to the target nucleic acid. In certain embodiments, the terminal region consists of 1-4 terminal nucleosides. In certain embodiments, the terminal nucleosides are at the 3' end. In certain embodiments, one or more of the terminal nucleosides are not complementary to the target nucleic acid.

Antisense mechanisms include any mechanism involving the hybridization of an oligonucleotide with target nucleic acid, wherein the hybridization results in a biological effect. In certain embodiments, such hybridization results in either target nucleic acid degradation or occupancy with concomitant inhibition or stimulation of the cellular machinery involving, for example, translation, transcription, or splicing of the target nucleic acid.

One type of antisense mechanism involving degradation of target RNA is Rnase H mediated antisense. Rnase H is a cellular endonuclease which cleaves the RNA strand of an RNA:DNA duplex. It is known in the art that single-stranded antisense compounds which are "DNA-like" elicit Rnase H activity in mammalian cells. Activation of Rnase H, therefore, results in cleavage of the RNA target, thereby greatly enhancing the efficiency of DNA-like oligonucleotide-mediated inhibition of gene expression.

Antisense mechanisms also include, without limitation RNAi mechanisms, which utilize the RISC pathway. Such RNAi mechanisms include, without limitation siRNA, ssRNA and microRNA mechanisms.

In certain embodiments, antisense compounds of the present invention are RNAi compounds. In certain embodiments, antisense compounds of the present invention are ssRNA compounds. In certain embodiments, antisense compounds of the present invention are paired with a second oligonucleotide to form an siRNA. In certain such embodiments, the second oligonucleotide is also a compound of the present invention. In certain embodiments, the second oligonucleotide is any modified or unmodified oligonucleotide. In certain embodiments, the oligonucleotide of the present invention is the antisense strand in an siRNA compound. In certain embodiments, the oligonucleotide of the present invention is the sense strand in an siRNA compound.

iv. Single-stranded RNAi Compounds

In certain embodiments, oligonucleotides of the present invention are particularly suited for use as single-stranded antisense compounds. In certain such embodiments, such oligonucleotides are single-stranded RNAi compounds. In certain embodiments, such oligonucleotides are ssRNA compounds or microRNA mimics Certain 5'-terminal nucleosides described herein are suited for use in such single-stranded oligonucleotides. In certain embodiments, such 5'-terminal nucleosides stabilize the 5'-phosphorous moiety. In certain embodiments, 5'-terminal nucleosides of the present invention are resistant to nucleases. In certain embodiments, the motifs of the present invention are particularly suited for use in single-stranded oligonucleotides. For further description of single-stranded RNAi compounds, see, e.g., WO 2010/048585, WO 2010/048549, and PCT/US2011/033968.

Use of single-stranded RNAi compounds has been limited. In certain instances, single stranded RNAi compounds are quickly degraded and/or do not load efficiently into RISC. Design of single-stranded RNAi compounds for use in cells and/or for use in vivo presents several challenges. For example, the compound must be chemically stable, resistant to nuclease degradation, capable of entering cells, capable of loading into RISC (e.g., binding Ago1 or Ago2), capable of hybridizing with a target nucleic acid, and not toxic to cells or animals. In certain instances, a modification or motif that improves one such feature may worsen another feature, rendering a compound having such modification or motif unsuitable for use as an RNAi compound. For example, certain modifications, particularly if placed at or near the 5'-end of an oligonucleotide, may make the compound more stable and more resistant to nuclease degradation, but may also inhibit or prevent loading into RISC by blocking the interaction with RISC components, such as Ago1 or Ago2. Despite its improved stability properties, such a compound would be unsuitable for use in RNAi.

In certain instances, a single-stranded oligonucleotide comprising a 5'-phosphorous moiety is desired. For example, in certain embodiments, such 5'-phosphorous moiety is necessary or useful for RNAi compounds, particularly, single-stranded RNAi compounds. In such instances, it is further desirable to stabilize the phosphorous moiety against degradation or de-phosphorylation, which may inactivate the compound. Further, it is desirable to stabilize the entire 5'-nucleoside from degradation, which could also inactivate the compound. Thus, in certain embodiments, oligonucleotides in which both the 5'-phosphorous moiety and the 5'-nucleoside have been stabilized are desired. In certain embodiments, provided are modified nucleosides that may be placed at the 5'-end of an oligonucleotide, resulting in a stabilized phosphorous and stabilized nucleoside. In certain such embodiments, the phosphorous moiety is resistant to removal in biological systems, relative to unmodified nucleosides and/or the 5'-nucleoside is resistant to cleavage by nucleases. In certain embodiments, such nucleosides are modified at one, at two or at all three of: the 2'-position, the 5'-position, and at the phosphorous moiety. Such modified nucleosides may be incorporated at the 5'-end of an oligonucleotide.

Although certain oligonucleotides described herein have particular use as single-stranded compounds, such compounds may also be paired with a second strand to create a double-stranded compound. In such embodiments, the second strand of the double-stranded duplex may or may not also be an oligonucleotide as described herein.

In certain embodiments, oligonucleotides as described herein interact with an aragonite protein (Ago). In certain embodiments, such oligonucleotides first enter the RISC pathway by interacting with another member of the pathway (e.g., dicer). In certain embodiments, oligonucleotides first enter the RISC pathway by interacting with Ago. In certain embodiments, such interaction ultimately results in antisense activity. In certain embodiments, provided are methods of activating Ago comprising contacting Ago with an oligonucleotide. In certain embodiments, such oligonucleotides comprise a modified 5'-phosphate group. In certain embodiments, provided are methods of modulating the expression or amount of a target nucleic acid in a cell comprising contacting the cell with an oligonucleotide capable of activating Ago, ultimately resulting in cleavage of the target nucleic acid. In certain embodiments, the cell is in an animal. In certain embodiments, the cell is in vitro. In certain embodiments, the methods are performed in the presence of manganese. In certain embodiments, the manganese is endogenous. In certain embodiments, the methods are performed in the absence of magnesium. In certain embodiments, the Ago is endogenous to the cell. In certain such embodiments, the cell is in an animal. In certain embodiments, the Ago is human Ago. In certain embodiments, the Ago is Ago2. In certain embodiments, the Ago is human Ago2.

In certain embodiments, provided are oligonucleotides having motifs (nucleoside motifs and/or linkage motifs) that result in improved properties. Certain such motifs result in single-stranded oligonucleotides with improved stability and/or cellular uptake properties while retaining antisense activity. For example, oligonucleotides having an alternating nucleoside motif and seven phosphorothioate linkages at the 3'-terminal end have improved stability and activity. Similar compounds that comprise phosphorothioate linkages at each linkage have further improved stability, but are not active as RNAi compounds, presumably because the additional phosphorothioate linkages interfere with the interaction of the oligonucleotide with the RISC pathway components (e.g., with Ago). In certain embodiments, the oligonucleotides having motifs herein result in single-stranded RNAi compounds having desirable properties. In certain embodiments, such oligonucleotides may be paired with a second strand to form a double-stranded RNAi compound. In such embodiments, the second strand of such double-stranded RNAi compounds may comprise a motif as described herein, may comprise another motif of modifications or may be unmodified.

It has been shown that in certain circumstances for single-stranded RNA comprising a 5'-phosphate group has RNAi activity but has much less RNAi activity if it lacks such 5'-phosphate group. The present inventors have recognized that in certain circumstances unmodified 5'-phosphate groups may be unstable (either chemically or enzymatically). Accordingly, in certain circumstances, it is desirable to modify the oligonucleotide to stabilize the 5'-phosphate. In certain embodiments, this is achieved by modifying the phosphate group. In certain embodiments, this is achieved by modifying the sugar of the 5'-terminal nucleoside. In certain embodiments, this is achieved by modifying the phosphate group and the sugar. In certain embodiments, the sugar is modified at the 5'-position, the 2'-position, or both the 5'-position and the 2'-position. As with motifs, above, in embodiments in which RNAi activity is desired, a phosphate stabilizing modification must not interfere with the ability of the oligonucleotide to interact with RISC pathway components (e.g., with Ago).

In certain embodiments, provided are oligonucleotides comprising a phosphate-stabilizing modification and a motif described herein. In certain embodiments, such oligonucleotides are useful as single-stranded RNAi compounds having desirable properties. In certain embodiments, such oligonucleotides may be paired with a second strand to form a double-stranded RNAi compound. In such embodiments, the second strand may comprise a motif as described herein, may comprise another motif of modifications or may be unmodified RNA.

In certain embodiments, provided are compounds and methods for antisense activity in a cell. In certain embodiments, the cell is in an animal. In certain embodiments, the animal is a human. In certain embodiments, provided are methods of administering a compound as described herein to an animal to modulate the amount or activity or function of one or more target nucleic acid.

In certain embodiments oligonucleotides comprise one or more motifs as described herein, but do not comprise a phosphate stabilizing modification. In certain embodiments, such oligonucleotides are useful for in vitro applications.

e. Expanded Repeat-Containing RNA

In certain embodiments, provided are compounds and methods for modulating the amount, activity or function of an expanded repeat-containing RNA. Such expanded repeat-containing RNA molecules have been associated with a number of diseases or disorders.

Certain normal wild-type RNA molecules comprise repeat regions, which, in certain instances can become expanded. In certain instances, the shorter repeat regions of wild type transcripts not associated with disease have secondary structure, making them relatively inaccessible for base pairing with a complementary nucleic acid. In contrast, the number of repeats in the expanded repeat region of an expanded repeat-containing RNA is typically at least 2 fold normal and often more (e.g., 3, 5, 10 fold, up to 100 or even more than 1000 fold). This expansion increases the likelihood that part of the repeat is, at least temporarily, more accessible to base pairing with a complementary nucleic acid molecule, relative to the wild type allele. Thus, even though certain compounds described herein comprise oligonucleotides complementary to a repeat sequence present in both wild-type and repeat-expanded transcripts, in certain embodiments, such compounds selectively hybridize to the disease-associated repeat-expanded transcript. In certain embodiments, such compounds as described herein are more selective and potent than prior compounds targeting repeat-expanded transcripts, see, e.g. U.S. Ser. No. 61/302,450; U.S. Ser. No. 61/405,157; PCT/US2011/024099; U.S. Ser. No. 61/302,454; U.S. Ser. No. 61/302,482; U.S. Ser. No. 61/405,130; and PCT/US2011/024019, which are herein incorporated by reference in the entirety. Such selectivity is beneficial for treating diseases associated with expanded repeat-containing RNA irrespective of the mechanism of reduction of the aberrant transcript.

Certain expanded repeat-containing RNA have been referred to in the art as "gain-of-function RNAs" for their ability to sequester hnRNPs and impair the normal action of RNA processing in the nucleus (see e.g., Cooper, T. (2009) Cell 136, 777-793; O'Rourke, J R (2009) J. Biol. Chem. 284 (12), 7419-7423, which are herein incorporated by reference in the entirety). Several disease states are associated with expanded repeat-containing RNA, some of which only occur once a threshold number of repeats within the expanded repeat-containing RNA is reached. In certain embodiments, provided herein are methods of reducing the activity, function, or amount of an expanded repeat-containing RNA having at least 10, 15, 20, 25, 30, 35, 40, 45, 50, 55, 60, 80, 90, 100, 200, 300, 400, 500, 1000, or more than 1000 copies of a repeating nucleotide unit.

In certain embodiments, provided herein compounds and methods for targeting or treating an expanded repeat-containing RNA, wherein the repeat may be CAG, CUG, and CCUG. In certain embodiments, provided herein compounds and methods for targeting or treating any of the disorders in the following non limiting table, which may be associated with a CAG, CUG, or CCUG repeat:

| DISEASE | REPEAT | AFFECTED GENE | COPY NUMBER (NORMAL) | COPY NUMBER (DISEASED) | Reference |
|---|---|---|---|---|---|
| Atrophin 1 (DRPLA) | CAG | ATN1/DRPLA | 7 to 34 | 49-93 | Nat. Genet. 10: 99, 1995 |
| Huntington disease | CAG | Htt | <28 | >36 | Lancet 369: 220, 2007 |

-continued

| DISEASE | REPEAT | AFFECTED GENE | COPY NUMBER (NORMAL) | COPY NUMBER (DISEASED) | Reference |
|---|---|---|---|---|---|
| Huntington disease-like 2 (HDL2) | CAG | junctophilin-3 (JPH3) | 6 to 28 | 44 to 57 | Nat. Clin Prac Neurol. 3: 517, 2007 |
| Spinal and bulbar muscular atrophy/Kennedy disease | CAG | Androgen receptor (AR) (X-linked) | 10 to 36 | 38 to 62 | Nature 352: 77, 1991 |
| Spinocerebellar ataxia 1 | CAG | ataxin-1 (ATXN1) | 6 to 35 | 49 to 88 | NCBI/OMIM |
| Spinocerebellar ataxia 12 | CAG | protein phosphatase PP2A (PPP2R2B) | 9 to 28 | 55 to 78 | Brain Res Bull. 56: 397, 2001 |
|  |  |  | 7 to 28 | 66 to 78 | Wikipedia |
| Spinocerebellar ataxia 17/Huntington disease-like 4 (HDL4) | CAG | TATA box-binding protein (TBP) | 25 to 42 | 47 to 63 | Eur. J. Hum. Genet. 9: 160, 2001 (NCBI/OMIM) |
| Spinocerebellar ataxia 2 | CAG | ATXN2 | 17 to 29 | 37 to 50 | Nat. Genet. 14: 285, 1996 (NCBI/OMIM) |
| Spinocerebellar ataxia 3 (Machado-Joseph disease | CAG | ATXN3 | 15 to 34 | 35 to 59 | Nat. Genet. 14: 277, 1996(NCBI/OMIM) |
|  |  |  | 14 to 32 | 33 to 77 | Wikipedia |
|  |  |  | 10 to 51 | 55-87 | Human Mol. Genet. 17: 2071, 2008 (NCBI/OMIM) |
|  |  |  | 12 to 40 | 55 to 86 | Wikipedia |
| Spinocerebellar ataxia 6 | CAG | CACNA1A | 4 to 18 | 21 to 30 | Wikipedia |
|  |  |  | 5 to 20 | 21 to 25 | Am. J. Hum. Genet. 61: 336, 1997 (NCBI/OMIM) |
| Spinocerebellar ataxia 7/OPCA3 | CAG | ATXN7 | 7 to 17 | 38-130 | Nat. Genet. 17: 65, 1997 (NCBI/OMIM) |
| Ataxin 8 opposite strand (ATXN8OS) | CUG with or without interruptions | SCA8/ataxin 8 | 16-37 | 107-127 | Nat. Genet 21: 379, 1999 (NCBI/OMIM) |
| Huntington disease-like 2 (HDL2) | CAG/CUG | junctophilin-3 (JPH3) | 6 to 28 | 44 to 57 | Nat. Clin Prac Neurol. 3: 517, 2007 |
| Myotonic dystrophy (DM1) | CUG | DMPK | 5 TO 35 | 80 TO >2500 | Harper, Myotonic Dystrophy (Saunders, London, ed. 3, 2001) |
|  |  |  |  | 50 to >3500 | Annu. Rev. Neurosci. 29: 259, 2006 |
|  |  |  | 5 to 37 | >50 | EMBO J. 19: 4439, 2000 |
|  |  |  |  | 50 to >2000 | Curr Opin Neurol. 20: 572, 2007 |
| DM2 | CCUG | zinc finger protein-9 |  | 75 to 11,000 | Science 293: 864, 2001 (NCBI/OMIM) |
| Spinocerebellar ataxia 8 | CUG | SCA8 |  | 74 to >1300 | Nat. Genet. 21: 379, 1999 |

In certain embodiments, compounds described herein are used to alter the activity or amount of expanded repeat-containing RNA and/or associated protein. In certain embodiments, compounds described herein are mutant selective. Accordingly, certain such compounds reduce the amount or activity of expanded repeat-containing RNA to a greater extent than they reduce the amount or activity of the corresponding wild-type RNA.

In certain embodiments, oligonucleotides described herein have a sequence comprising a hybridizing region having one mismatch relative to the target repeat. In certain embodiments, oligonucleotides comprise a hybridizing region having two mismatches relative to the target repeat. In certain embodiments, oligonucleotides comprise a hybridizing region having three mismatches relative to the target repeat. In certain embodiments, oligonucleotides comprise a hybridizing region having four or more mismatches relative to the target repeat. In certain embodiment, at least one mismatch is at position 7, 8, 9, 10, or 11, counting from the 5'-end of the hybridizing region. In certain embodiments, at least one mismatch is at position 9, 10, 11, 12, or 13, counting from the 3'-end of the hybridizing region. In certain embodiment, at least one mismatch is at position 7, 8, 9, 10, or 11, counting from the 5'-end of the hybridizing region and position 9, 10, 11, 12, or 13, counting from the 3'-end of the hybridizing region. In certain embodiment, at least one mismatch is at position 7, 8, 9, 10, or 11, counting from the 5'-terminal nucleotide and position 9, 10, 11, 12, or 13, counting from the 3'-end terminal nucleotide. In certain embodiment, at least one mismatch is at position 3, 8, 13, and 17, counting from the 5'-terminal nucleotide. In certain embodiment, at least one mismatch is at position 4, 10, and 16, counting from the 5'-terminal nucleoside. In certain embodiment, at least one mismatch is at position 9 and 11, counting from the 5'-terminal nucleoside. In certain embodiment, at least one mismatch is at position 9 and 12, counting from the 5'-terminal nucleoside. In certain embodiment, at least one mismatch is at position 9 and 13, counting from the 5'-terminal nucleoside. In certain embodiment, at least one mismatch is at position 9 and 14, counting from the 5'-terminal nucleoside. In certain embodiment, at least one mismatch is at position 9 and 15, counting from the 5'-terminal nucleoside. In certain embodiment, at least one mismatch is at position 9 and 16, counting from the 5'-terminal nucleoside. In certain embodiment, at least one mismatch is at position 9 and 17, counting from the 5'-terminal nucleoside. In certain embodiment, at least one mismatch is at position 9 and 18, counting from the 5'-terminal nucleoside. In certain embodiments, such mismatches may result in the resulting duplex being processed differently by the cell. For example, such mismatched duplexes resemble microRNA, rather than siRNA. Thus, in certain instances, such molecules track the microRNA pathway, ending in sequestration, rather than siRNA-like cleavage. In certain circumstances, utilization of the microRNA pathway may result in greater selectivity for mutant over wild-type.

In certain embodiments, provided are methods of modulating the expression or amount of a target nucleic acid in a cell comprising contacting the cell with an oligonucleotide having a sequence comprising a hybridizing region having one or more mismatches relative to the target and capable of activating Ago. In certain embodiments, although the oligonucleotide activates Ago, the oligonucleotide's mismatches may prevent Ago from cleaving target mRNA. In certain embodiments, although the oligonucleotide activates Ago, the oligonucleotide's mismatches may disrupt AGO-mediated cleavage of mRNA and may result in an oligonucleotide-AGO complex that blocks ribosomal activity and inhibits protein translation. In certain embodiments, although the oligonucleotide interacts with Ago, the oligonucleotide's mismatches may prevent translation of the mRNA. In certain embodiments, oligonucleotides having a sequence comprising a hybridizing region having one or more mismatches relative to the target may prevent translation of the target mRNA. In certain embodiments, oligonucleotides having a sequence comprising a hybridizing region having one or more mismatches relative to the target may prevent translation of a mutant mRNA containing one or more nucleotide repeats.

In certain embodiments, a mutant allele may have more nucleotide repeats than a wild type allele. In certain embodiments, the expanded number of nucleotide repeats offers more binding sites for complementary oligonucleotides. For example, a mutant allele may have many more repeats than the wild type allele and the mutant allele may therefore bind more complementary oligonucleotides than the wild type allele. In certain embodiments, for example, mutant HTT mRNA may have 69 or more repeats whereas a wild-type HTT mRNA may have 17 repeats. A mutant HTT mRNA having 69 repeats can bind up to 9-10 twenty base long oligomers whereas the wild type HTT mRNA may only bind one or two twenty base long oligomers. In certain embodiments, the binding of multiple oligomers within a mutant repeat region can produce cooperative inhibition and produce selective inhibition of the mutant allele compared to the wild type allele.

In certain embodiments, the expanded number of nucleotide repeats present in mutant alleles may form structures that differ from the structure of the wild-type allele. In certain embodiments, structure of a mutant allele may facilitate recognition by an oligonucleotide. In certain embodiments, an oligomeric compound may more readily interact with a mutant allele as compared to a wild-type allele. For example, in certain embodiments, a mutant HTT mRNA having 69 repeats may comprise a structure that facilitates interaction with an oligomeric compound, whereas a wild type HTT mRNA may comprise a structure that does not facilitate interaction with said oligomeric compound. In certain such instances, certain oligomeric compounds may selectively reduce expression of a mutant allele compared to a wild-type allele.

Dentatorubral-pallidoluysian atrophy (DRPLA) is an inherited autosomal dominant disorder. DRPLA is a neurodegenerative disease with clinical manifestations that include dementia, ataxia, epilepsy, chorea, and psychological disturbances. DRPLA is caused by an expansion of the CAG repeat region within the atrophin-1 (ATN-1) gene from a normal value of under 34 repeats to up to 90 in DRPLA patients. The mean repeat number is estimated at 63-68 repeats.

In certain embodiments, the expanded number of nucleotide repeats present in mutant alleles may form structures that differ from the structure of the wild-type allele. In certain embodiments, structure of a mutant allele may facilitate recognition by an oligonucleotide. In certain embodiments, an oligomeric compound may more readily interact with a mutant allele as compared to a wild-type allele. For example, in certain embodiments, a mutant ATN-1 mRNA having more than 34 repeats may comprise a structure that facilitates interaction with an oligomeric compound, whereas a wild type ATN-1 mRNA may comprise a structure that does not facilitate interaction with said oligomeric compound. In certain such instances, certain oligomeric compounds may selectively reduce expression of a mutant allele (e.g. an ATN-1 allele having more than 34 repeats) compared to a wild-type allele.

C. Certain Pharmaceutical Compositions

In certain embodiments, provided herein are pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligonucleotide which are cleaved by endogenous nucleases within the body, to form the active antisense oligonucleotide.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents as described herein to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection or infusion (e.g., intravenous, subcutaneous, intramuscular, intrathecal, intracerebroventricular etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, provided herein are compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human.

In certain embodiments, provided herein are methods of administering a pharmaceutical composition comprising an oligonucleotide as described herein to an animal. Suitable administration routes include, but are not limited to, oral, rectal, transmucosal, intestinal, enteral, topical, suppository, through inhalation, intrathecal, intracerebroventricular, intraperitoneal, intranasal, intraocular, intratumoral, and parenteral (e.g., intravenous, intramuscular, intramedullary, and subcutaneous).

D. Certain Uses and Routes of Administration

In certain embodiments, provided herein are methods of contacting a cell with an oligonucleotide described herein. In certain embodiments, the cell is in vitro. In certain embodiments, the cell is in an animal (e.g., rodent, primate, monkey or human). In certain embodiments, antisense activity is detected.

In certain embodiments, the disease is any of atrophin 1 (DRPLA), Huntington's Disease, Huntington disease-like 2 (HDL2), spinal and bulbar muscular atrophy, Kennedy disease, spinocerebellar ataxia 1, spinocerebellar ataxia 12, spinocerebellar ataxia 17, Huntington disease-like 4 (HDL4), spinocerebellar ataxia 2, spinocerebellar ataxia 3, Machado-Joseph disease, spinocerebellar ataxia 6, spinocerebellar ataxia 7 (OPCA3), ataxin 8 opposite strand (ATXN8OS), myotonic dystrophy (DM1), DM2, and spinocerebellar ataxia 8.

In certain embodiments, compounds as described herein are administered to an animal (e.g., a human) to provide a therapeutic effect. Certain diseases or disorders have been identified to be associated with expanded repeat-containing RNA. Any such disease or disorder might be treated with compounds as described herein. In certain embodiments, the disease is selected from among: ataxin 8, atrophin 1, fragile X syndrome, Friedrich's ataxia, Huntington's disease, Huntington's disease-like 2, myotonic dystrophy, spinal and bulbar muscular atrophy, and spinocerebellar ataxia. In certain embodiments, the disease is Huntington's disease. In certain embodiments, the disease is myotonic dystrophy. In certain embodiments, the myotonic dystrophy is myotonic dystrophy type 1. In certain embodiments, the myotonic dystrophy is myotonic dystrophy type 2. In certain embodiments, the disease is spinocerebellar ataxia. In certain embodiments, the spinocerebellar ataxia is spinocerebellar ataxia 10. In certain embodiments, the spinocerebellar ataxia is spinocerebellar ataxia 3, also known as Machado-Joseph disease.

In certain embodiments, pharmaceutical compositions as described herein are administered to a subject. In certain embodiments, such pharmaceutical compositions are administered by injection. In certain embodiments, such pharmaceutical compositions are administered by infusion.

In certain embodiments, pharmaceutical compositions are administered by injection or infusion into the CSF. In certain such embodiments, pharmaceutical compositions are administered by direct injection or infusion into the spine. In certain embodiments, pharmaceutical compositions are administered by injection or infusion into the brain. In certain embodiments, pharmaceutical compositions are administered by intrathecal injection or infusion rather than into the spinal cord tissue itself. Without being limited as to theory, in certain embodiments, the antisense compound released into the surrounding CSF and may penetrate into the spinal cord parenchyma. An additional advantage of intrathecal delivery is that the intrathecal route mimics lumbar puncture administration (i.e., spinal tap) already in routine use in humans.

In certain embodiments, pharmaceutical compositions are administered by intracerebroventricular (ICV) injection or infusion. Intracerebroventricular or intraventricular delivery of a pharmaceutical composition comprising one or more oligonucleotide may be performed in any one or more of the brain's ventricles, which are filled with cerebrospinal fluid (CSF). CSF is a clear fluid that fills the ventricles, is present in the subarachnoid space, and surrounds the brain and spinal cord. CSF is produced by the choroid plexuses and via the weeping or transmission of tissue fluid by the brain into the ventricles. The choroid plexus is a structure lining the floor of the lateral ventricle and the roof of the third and fourth ventricles. Certain studies have indicated that these structures are capable of producing 400-600 ccs of fluid per day consistent with an amount to fill the central nervous system spaces four times in a day. In adult humans, the volume of this fluid has been calculated to be from 125 to 150 ml (4-5 oz). The CSF is in continuous formation, circulation and absorption. Certain studies have indicated that approximately 430 to 450 ml (nearly 2 cups) of CSF may be produced every day. Certain calculations estimate that production equals approximately 0.35 ml per minute in adults and 0.15 per minute in infant humans. The choroid plexuses of the lateral ventricles produce the majority of CSF. It flows through the foramina of Monro into the third ventricle where it is added to by production from the third ventricle and continues down through the aqueduct of Sylvius to the fourth ventricle. The fourth ventricle adds more CSF; the fluid then travels into the subarachnoid space through the foramina of Magendie and Luschka. It then circulates throughout the base of the brain, down around the spinal cord and upward over the cerebral hemispheres. The CSF empties into the blood via the arachnoid villi and intracranial vascular sinuses.

In certain embodiments, such pharmaceutical compositions are administered systemically. In certain embodiments, pharmaceutical compositions are administered subcutaneously. In certain embodiments, pharmaceutical compositions are administered intravenously. In certain embodiments, pharmaceutical compositions are administered by intramuscular injection.

In certain embodiments, pharmaceutical compositions are administered both directly to the CSF (e.g., IT and/or ICV injection and/or infusion) and systemically. In certain such embodiments, compounds as described herein have one or more desirable properties making them suitable for such administration. Drug design typically requires a balance of several variables, including, but not limited to: potency, toxicity, stability, tissue distribution, convenience, and cost of a candidate compound. Such balancing is influenced by a number of factors, including the severity and typical duration of the disease treated. For example, greater drug-related toxicity is tolerated for use in treating acute lethal diseases than chronic sub-lethal diseases. In certain embodiments, compounds as described herein will have one or more improved properties compared to similar compounds that lack certain features as described herein. For example, compared to other compounds, the compounds as described herein, may, in certain embodiments, have improved potency or may have similar potency but reduced toxicity and consequently improved therapeutic index. In certain embodiments, compounds as described herein may have improved pharmacokinetics or distribution to a particular desired target tissue.

In certain embodiments, oligonucleotides as described herein are used in cells in vitro. In certain such embodiments, such uses are to identify and/or study expanded repeat-containing nucleic acids and mechanisms surrounding them and associated diseases.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine(methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligonucleotide having the nucleobase sequence "ATCGATCG" encompasses any oligonucleotides having such nucleobase sequence, whether modified or unmodified, including, but not limited to, such compounds comprising RNA bases, such as those having sequence "AUCGAUCG" and those having some DNA bases and some RNA bases such as "AUCGATCG" and oligonucleotides having other modified bases, such as "AT$^{me}$CGAUCG," wherein $^{me}$C indicates a cytosine base comprising a methyl group at the 5-position.

EXAMPLES

Non-limiting Disclosure and Incorporation by Reference

While certain compounds, compositions and methods described herein have been described with specificity in accordance with certain embodiments, the following examples serve only to illustrate the compounds described herein and are not intended to limit the same. Each of the patents, applications, printed publications, and other published documents mentioned or referred to in this specification are herein incorporated by reference in their entirety.

General Methods
Synthesis of ss-siRNAs ssRNA syntheses were performed on ABI 394 synthesizer (1-2 mmol scale) by the phosphoramidite coupling method on an UnyLinker solid support packed in the column A 0.1M solution of 20-F, 20-O-Me and 20-O-MOE nucleoside phosphoramidites in anhydrous CH3CN were used for the synthesis. For the coupling step, the phosphoramidites were delivered 6-9-fold excess over the loading on the solid support, and phosphoramidite condensation was carried out for 10 min. All other steps in the protocol supplied by manufacturer were used. A solution of 3% dichloroacetic acid in dichloromethane was used for removing dimethoxytrityl group from 50-hydroxyl group of the nucleotide. Extended detritylation condition was used to remove the dimethoxytrityl group from the secondary hydroxyl group of the UnyLinker solid support. The 4,5-Dicyanoimidazole (0.7 M) in anhydrous CH3CN was used as activator during coupling step. PS linkages were introduced using 0.2M solution of phenylacetyl disulfide in 1:1 pyridine/CH3CN as sulfur transfer reagent and treated for 3 min. A solution of tert-butyl hydroperoxide/acetonitrile/water (10:87:3) was used to introduce phosphodiester linkages and treated for 12 min Chemical phosphorylation reagent procured form Glen Research Inc., Virginia, USA was used to phosphorylate the 50-terminus of ss-siRNAs. The step-wise coupling efficiencies were >97%. After completion of the synthesis, solid support was suspended in aqueous ammonium (28-30 wt. %) and heated at 55_C for 6 h. The reaction mixture was allowed to come to room temperature, and the solid support was filtered and washed with water. The washing and filtrate were combined together and evaporated to dryness. The residue obtained was dissolved in water and purified by High Performance Liquid Chromatography (HPLC) on a strong anion exchange column (Mono Q, GE Healthcare, 16/10, 20 ml, 10 mm, ionic capacity 0.27-0.37 mmol/ml, A=100 mM ammonium acetate, 30% aqueous acetonitrile, B=1.5M NaBr in A, 0-60% B in 40 min, Flow 1.5 ml min_1, _=260 nm). Desalting by HPLC on a reverse phase column gave ss-siRNAs in an isolated yield of 15-30% based on the initial loading on the solid support. sssiRNAs were characterized by ion-pair-HPLC coupled MS analysis with Agilent 1100 MSD system.

Cell Culture and Transfection ss-siRNAs and bridged nucleic acids (BNAs) were synthesized and reconstituted in nuclease-free water. Patient-derived fibroblast cell lines GM06151 were obtained from the Coriell Institute (Camden, N.J.). The fibroblasts were maintained at 37_C and 5% CO2 in Minimal Essential Media Eagle (Sigma, M4655) supplemented with 10% heat inactivated fetal bovine serum (Sigma) and 0.5% Minimal Essential Media Eagle non-essential amino acids (Sigma). Cells were plated at a density of 70,000 per well of a 6-well plate 48 h before transfection. siRNAs were transfected into cells with lipid RNAiMAX (Invitrogen) as previously described. Cells were typically harvested 3 days after transfection for qPCR or 4 days for protein assay. For double transfection experiments, the first transfection was performed as described. Media was changed 24 h later, and cells were split into new 6-well plate after 72 h of transfection. The second transfection was carried out on the next day. Media was changed again after 24 h, and cells were harvested after 96 h of second transfection for protein analysis.

Western Blot and PCR Analysis

In all, 7.5% or 4-20% acrylamide pre-cast gels (Bio-Rad) were used to separate the ATX-3 isoforms. The primary antibodies were used: anti-ATX-3 (MAB5360, Millipore), anti-ATX-3 polyclonal antibody (from Dr Henry Paulson, University of Michigan), anti-polyQ monoclonal antibody (5TF1-1C2, Millipore, MAB1574) and antib-actin (Sigma). Protein bands were quantified using ImageJ software. The percentage of inhibition was calculated as a relative value to a control sample. Dose fitting curve was generated using GraphPad Prism 4 program by the equation: $y=100[1-x^m/(n^m+x^m)]$, where y is percentage of inhibition, and x is the siRNA concentration, n is the IC50 value, and m is the Hill coefficient value. All the experiments were repeated for at least three times, and the error bar is standard deviation. Quantitative PCR was performed on a 7500 real-time PCR system (Applied Biosystems) using iTaq SYBR Green Supermix (Bio-rad). Data were normalized relative to levels of GAPDH mRNA. The following A10Q5 5 qPCR primers were used: 5'-GGAAATATGGATGACAGTGG-3' (SEQ ID NO. 1) (F); 5'-ATCCTGAGCCTCTGATACTC-3'(R) (SEQ ID NO. 2). GAPDH primers were obtained from Applied Biosystems. The qPCR cycles are as follows: 50_C for 2 min; 95_C for 5 min; (95_C for 15 s; 60_C for 1 min)×40 cycles. Experiments were performed in biological triplicate and error reported as standard deviation. For RTPCR, the amplification was performed using LA Taq DNA polymerase (TaKaRa) using the following primers to detect the spliced band of ATX-3: P8 primer pair 5'-GATGAG-GAAGCAGATCTCCGCAGGG-3' (SEQ ID NO. 3) (8F), 5'-CTA AAGACATGGTCACAGCTGCCTGAAGC-3' (SEQ ID NO. 4) (8R); P10 primer pair 5'-GATTTGCA-GAGGGCTCTGGCACTAAGTC-3' (SEQ ID NO. 5) (10F) and 5'-AGCATGTCTTCTTCACTCATAGCAT-CACTTTTC-3'(10R) (SEQ ID NO. 6). The PCR products were separated on 1.5% agarose gels and visualized on an AlphaImager.

RNA Immunoprecipitation

SCA3 fibroblast cells were seeded at 1400K in 150 cm2 dishes. Duplex RNAs were transfected with RNAiMAX in the next day. Cells were harvested 72 h later and were lysed in a buffer [20 mM Tris-HCl (pH7.4) 150 mM NaCl, 2 mM MgCl2, 0.5% NP-40, 0.5 mM DTT, protease inhibitor (EDTA-free, Roche) and RNase inhibitor (Promega, 50 U/ml final)] with a volume about three times of the cell pellet size. The mixture was sat on ice for 10 min after AQ6 thorough mixing. After centrifugation, the supernatant were isolated and stored at _80_C. Sixty microliters of Protein A/G agarose Plus was incubated with 4 ml of antibodies (anti-AGO2, 4G8, 011-22033, Wako; anti-GW-182, A302-329A, Bethyl Laboratories; or mouse IgG, 12-371, Millipore) in 1_PBS (pH 7.4) at 4_C with gentle agitation for 2 h. After two washes of 1_PBS, beads were incubated with cell lysate for 2 h at 4_C. The beads were extensively washed with aforementioned lysis buffer once, IP wash buffer twice [300 mM NaCl, 3 mM MgCl2, 0.5% NP-40 and 20 mM Tris-HCl (pH 7.4) and 1_PBS once. The beads were finally eluted with elution buffer (1% SDS, 0.1M NaHCO3 and RNase inhibitor]. After proteinase K treatment, RNA extraction and precipitation, samples were treated with recombinant DNase I, followed by reverse transcription. The mRNA levels were quantified by qPCR. Results were normalized first by GAPDH levels and second by that of IgG.

Example 1

Design of Modified Single Stranded RNAs (ssRNAs) Targeting Ataxin-3 CAG Repeat Region Modified ssRNAs, siRNAs and gapmers are described in the tables below. A subscript "s" between two nucleosides indicates a phosphorothioate internucleoside linkage (going 5' to 3'). The absence of a subscript "s" between two nucleosides indicates a phosphodiester internucleoside linkage. A "Pv" at the 5'-end indicates a 5'-(E)-vinylphosphonate group, $(PO(OH)_2(CH=CH-)$. A "Po" at the 5'-end indicates a 5'-phosphate group, $(PO(OH)_2-)$. Nucleosides without a subscript are β-D-2'-deoxyribonucleosides. Nucleosides with an "r" subscript are ribonucleosides. Nucleosides followed by a subscript "f", "m" or "e" are sugar modified nucleosides. A subscript "f" indicates a 2'-fluoro modified nucleoside, a subscript "m" indicates a 2'-O-methyl modified nucleoside and a subscript "e" indicates a 2'-O-methoxyethyl (MOE) modified nucleoside. $^{me}C$ indicates a 5-methyl cytosine nucleoside. Unless otherwise indicated, underlined nucleosides indicate the mismatch position.

TABLE 1

Modified ssRNAs targeting Ataxin-3 CAG repeat region

| ISIS No. | Sequence 5'-3' | Mismatch Position from 5'-end | Seq ID NO. |
|---|---|---|---|
| 556886 | 5'-Po-$T_{es}C_{fs}U_{mo}A_{fs}C_{mo}U_{fs}G_{mo}C_{fs}U_{mo}G_{fs}C_{mo}U_{fs}G_{mo}C_{fs}U_{ms}G_{fs}C_{ms}U_{fs}G_{ms}A_{es}A_e$ | 4 | 7 |
| 556887 | 5'-Po-$T_{es}C_{fs}U_{mo}G_{fs}A_{mo}U_{fs}G_{mo}C_{fs}U_{mo}G_{fs}C_{mo}U_{fs}G_{mo}C_{fs}U_{ms}G_{fs}C_{ms}U_{fs}G_{ms}A_{es}A_e$ | 5 | 8 |
| 556888 | 5'-Po-$T_{es}C_{fs}U_{mo}G_{fs}C_{mo}A_{fs}G_{mo}C_{fs}U_{mo}G_{fs}C_{mo}U_{fs}G_{mo}C_{fs}U_{ms}G_{fs}C_{ms}U_{fs}G_{ms}A_{es}A_e$ | 6 | 9 |
| 556889 | 5'-Po-$T_{es}C_{fs}U_{mo}G_{fs}C_{mo}U_{fs}A_{mo}C_{fs}U_{mo}G_{fs}C_{mo}U_{fs}G_{mo}C_{fs}U_{ms}G_{fs}C_{ms}U_{fs}G_{ms}A_{es}A_e$ | 7 | 10 |
| 556890 | 5'-Po-$T_{es}C_{fs}U_{mo}G_{fs}C_{mo}U_{fs}G_{mo}A_{fs}U_{mo}G_{fs}C_{mo}U_{fs}G_{mo}C_{fs}U_{ms}G_{fs}C_{ms}U_{fs}G_{ms}A_{es}A_e$ | 8 | 11 |
| 553822 | 5'-Po-$T_{es}C_{fs}U_{mo}G_{fs}C_{mo}U_{fs}G_{mo}C_{fs}A_{mo}G_{fs}C_{mo}U_{fs}G_{mo}C_{fs}U_{ms}G_{fs}C_{ms}U_{fs}G_{ms}A_{es}A_e$ | 9 | 12 |
| 553821 | 5'-Po-$T_{es}C_{fs}U_{mo}G_{fs}C_{mo}U_{fs}G_{mo}C_{fs}U_{mo}A_{fs}C_{mo}U_{fs}G_{mo}C_{fs}U_{ms}G_{fs}C_{ms}U_{fs}G_{ms}A_{es}A_e$ | 10 | 13 |
| 557407 | 5'-Po-$T_{es}C_{fs}U_{mo}G_{fs}C_{mo}U_{fs}G_{mo}C_{fs}U_{mo}G_{fs}C_{mo}U_{fs}G_{mo}C_{fs}U_{ms}G_{fs}C_{ms}U_{fs}G_{ms}A_{es}A_e$ | 10 | 14 |
| 556891 | 5'-Po-$T_{es}C_{fs}U_{mo}G_{fs}C_{mo}U_{fs}G_{mo}C_{fs}U_{mo}G_{fs}A_{mo}U_{fs}G_{mo}C_{fs}U_{ms}G_{fs}C_{ms}U_{fs}G_{ms}A_{es}A_e$ | 11 | 15 |
| 556892 | 5'-Po-$T_{es}C_{fs}U_{mo}G_{fs}C_{mo}U_{fs}G_{mo}C_{fs}U_{mo}G_{fs}C_{mo}A_{fs}G_{mo}C_{fs}U_{ms}G_{fs}C_{ms}U_{fs}G_{ms}A_{es}A_e$ | 12 | 16 |
| 557406 | 5'-Po-$T_{es}C_{fs}U_{mo}G_{fs}C_{mo}U_{fs}G_{mo}C_{fs}U_{mo}G_{fs}C_{mo}U_{fs}A_{mo}C_{fs}U_{ms}G_{fs}C_{ms}U_{fs}G_{ms}A_{es}A_e$ | 13 | 17 |

TABLE 1-continued

Modified ssRNAs targeting Ataxin-3 CAG repeat region

| ISIS No. | Sequence 5'-3' | Mismatch Position from 5'-end | Seq ID NO. |
|---|---|---|---|
| 557408 | 5'-Po-$T_{es}C_{fs}U_{mo}G_{fs}C_{mo}U_{fs}G_{mo}C_{fs}U_{mo}G_{mo}C_{fs}U_{ms}A_{fs}C_{ms}U_{fs}G_{ms}A_{es}A_e$ | 16 | 18 |
| 557409 | 5'-Po-$T_{es}C_{fs}U_{mo}G_{fs}C_{mo}U_{fs}G_{mo}C_{fs}A_{mo}A_{fs}C_{mo}U_{fs}G_{mo}C_{fs}U_{ms}G_{fs}C_{ms}U_{fs}G_{ms}A_{es}A_e$ | 9, 10 | 19 |
| 557426 | 5'-Po-$T_{es}C_{fs}U_{mo}G_{fs}C_{mo}U_{fs}G_{mo}C_{fs}A_{mo}A_{fs}A_{mo}U_{fs}G_{mo}C_{fs}U_{ms}G_{fs}C_{ms}U_{fs}G_{ms}A_{es}A_e$ | 9, 10, 11 | 20 |
| 557427 | 5'-Po-$T_{es}C_{fs}U_{mo}G_{fs}C_{mo}U_{fs}G_{mo}A_{fs}A_{mo}A_{fs}A_{mo}U_{fs}G_{mo}C_{fs}U_{ms}G_{fs}C_{ms}U_{fs}G_{ms}A_{es}A_e$ | 8, 9, 10, 11 | 21 |
| 557428 | 5'-Po-$T_{es}C_{fs}U_{mo}A_{fs}C_{mo}U_{fs}G_{mo}C_{fs}U_{mo}A_{fs}C_{mo}U_{fs}G_{mo}C_{fs}U_{ms}A_{fs}C_{ms}U_{fs}G_{ms}A_{es}A_e$ | 4, 10, 16 | 22 |
| 557429 | 5'-Po-$T_{es}C_{fs}A_{mo}G_{fs}C_{mo}U_{fs}G_{mo}U_{fs}G_{mo}C_{fs}U_{mo}A_{fs}C_{ms}U_{fs}G_{ms}U_{fs}G_{ms}A_{es}A_e$ | 3, 8, 13, 17 | 23 |
| 557430 | 5'-Po-$T_{es}G_{fs}C_{mo}U_{fs}G_{mo}C_{fs}U_{mo}G_{fs}C_{mo}U_{fs}G_{mo}C_{fs}U_{mo}G_{fs}Cms U_{fs}G_{ms}C_{fs}U_{ms}A_{es}A_e$ | None | 24 |
| 537775 | 5'-Pv-$T_{es}C_{fs}U_mG_{fs}C_mU_{fs}G_mC_{fs}\underline{A}_nG_{fs}C_mU_{fs}G_m C_{fs}U_{ms}G_{fs}C_{ms}U_{fs}G_{ms}A_{es}A_e$-3' | 9 | 12 |

TABLE 2

Modified ssRNAs of varying length targeting Ataxin-3 CAG repeat region

| ISIS No. | Sequence 5'-3' | Length | Seq ID NO. |
|---|---|---|---|
| 553822 | 5'-Po-$T_{es}C_{fs}U_{mo}G_{fs}C_{mo}U_{fs}G_{mo}C_{fs}\underline{A}_{mo}G_{fs}C_{mo}U_{fs}G_{mo}C_{fs}U_{ms}G_{fs}C_{ms}U_{fs}G_{ms}A_{es}A_e$ | 21 | 12 |
| 581440 | 5'-Po-$T_{es}C_{fs}U_{mo}G_{fs}C_{mo}U_{fs}G_{mo}C_{fs}\underline{A}_{mo}G_{fs}C_{mo}U_{fs}G_{mo}C_{fs}U_{ms}G_{fs}C_{es}U_{fs}A_{es}A_e$ | 20 | 25 |
| 581441 | 5'-Po-$T_{es}C_{fs}U_{mo}G_{fs}C_{mo}U_{fs}G_{mo}C_{fs}\underline{A}_{mo}G_{fs}C_{mo}U_{fs}G_{ms}C_{fs}U_{ms}G_{fs}C_{ms}A_{es}A_e$ | 19 | 26 |
| 581449 | 5'-Po-$T_{es}C_{fs}U_{mo}G_{fs}C_{mo}U_{fs}G_{mo}C_{fs}\underline{A}_{mo}G_{fs}C_{mo}U_{fs}G_{ms}C_{fs}U_{ms}G_{fs}A_{es}A_e$ | 18 | 27 |
| 581450 | 5'-Po-$T_{es}C_{fs}U_{mo}G_{fs}C_{mo}U_{fs}G_{mo}C_{fs}\underline{A}_{mo}G_{fs}C_{ms}U_{fs}G_{ms}C_{fs}U_{ms}A_{es}A_e$ | 17 | 28 |
| 581444 | 5'-Po-$T_{es}C_{fs}U_{mo}G_{fs}C_{mo}U_{fs}G_{mo}C_{fs}\underline{A}_{mo}G_{fs}C_{ms}U_{fs}G_{ms}C_{fs}A_{es}A_e$ | 16 | 29 |
| 581445 | 5'-Po-$T_{es}C_{fs}U_{mo}G_{fs}C_{mo}U_{fs}G_{mo}C_{fs}\underline{A}_{mo}G_{fs}C_{ms}U_{fs}G_{ms}A_{es}A_e$ | 15 | 30 |

TABLE 3

Modified ssRNAs targeting Ataxin-3 CAG repeat region

| ISIS No. | Sequence 5'-3' | Mismatch Position from 5'-end | Tm, °C. (single strand) | Seq ID NO |
|---|---|---|---|---|
| 641381 | 5'-Po-$T_{es}C_{fs}U_{mo}G_{fs}C_{mo}U_{fs}G_{mo}C_{fs}A_{mo}G_{fs}A_{mo}U_{fs}G_{mo}C_{fs}U_{ms}G_{fs}C_{ms}U_{fs}G_{ms}A_{es}A_e$ | 9, 11 | 65.9 | 31 |
| 641382 | 5'-Po-$T_{es}C_{fs}U_{mo}G_{fs}C_{mo}U_{fs}G_{mo}C_{fs}A_{mo}G_{fs}C_{mo}A_{fs}G_{mo}C_{fs}U_{ms}G_{fs}C_{ms}U_{fs}G_{ms}A_{es}A_e$ | 9, 12 | 77.4 | 32 |
| 641383 | 5'-Po-$T_{es}C_{fs}U_{mo}G_{fs}C_{mo}U_{fs}G_{mo}C_{fs}A_{mo}G_{fs}C_{mo}U_{fs}A_{mo}C_{fs}U_{ms}G_{fs}C_{ms}U_{fs}G_{ms}A_{es}A_e$ | 9, 13 | 71.1 | 33 |
| 618385 | 5'-Po-$T_{es}C_{fs}U_{mo}G_{fs}C_{mo}U_{fs}G_{mo}C_{fs}A_{mo}G_{fs}C_{mo}U_{fs}G_{mo}A_{fs}U_{ms}G_{fs}C_{ms}U_{fs}G_{ms}A_{es}A_e$ | 9, 14 | 62.6 | 34 |
| 618386 | 5'-Po-$T_{es}C_{fs}U_{mo}G_{fs}C_{mo}U_{fs}G_{mo}C_{fs}A_{mo}G_{fs}C_{mo}U_{fs}G_{mo}C_{fs}A_{ms}G_{fs}C_{ms}U_{fs}G_{ms}A_{es}A_e$ | 9, 15 | 87.1 | 35 |
| 618387 | 5'-Po-$T_{es}C_{fs}U_{mo}G_{fs}C_{mo}U_{fs}G_{mo}C_{fs}A_{mo}G_{fs}C_{mo}U_{fs}G_{mo}C_{fs}U_{ms}C_{fs}C_{ms}U_{fs}G_{ms}A_{es}A_e$ | 9, 16 | 63.7 | 36 |

TABLE 3-continued

Modified ssRNAs targeting Ataxin-3 CAG repeat region

| ISIS No. | Sequence 5'-3' | Mismatch Position from 5'-end | Tm, °C. (single strand) | Seq ID NO |
|---|---|---|---|---|
| 618388 | 5'-Po-T$_{es}$C$_{fs}$U$_{mo}$G$_{fs}$C$_{mo}$U$_{fs}$G$_{mo}$C$_{fs}$A$_{mo}$G$_{fs}$C$_{mo}$U$_{fs}$G$_{mo}$C$_{fs}$U$_{ms}$G$_{fs}$A$_{ms}$U$_{fs}$G$_{ms}$A$_{es}$A$_e$ | 9, 17 | 61.4 | 37 |
| 618389 | 5'-Po-T$_{es}$C$_{fs}$U$_{mo}$G$_{fs}$C$_{mo}$U$_{fs}$G$_{mo}$C$_{fs}$A$_{mo}$G$_{fs}$C$_{mo}$U$_{fs}$G$_{mo}$C$_{fs}$U$_{ms}$G$_{fs}$C$_{ms}$A$_{fs}$G$_{ms}$A$_{es}$A$_e$ | 9, 18 | 79.6 | 38 |
| 641384 | 5'-Po-T$_{es}$C$_{fs}$U$_{mo}$G$_{fs}$C$_{mo}$U$_{fs}$G$_{mo}$C$_{fs}$A$_{mo}$G$_{fs}$C$_{mo}$U$_{fs}$G$_{mo}$C$_{fs}$C$_{ms}$G$_{fs}$C$_{ms}$U$_{fs}$G$_{ms}$A$_{es}$A$_e$ | 9, 15 | 62.8 | 39 |
| 641385 | 5'-Po-T$_{es}$C$_{fs}$U$_{mo}$G$_{fs}$C$_{mo}$U$_{fs}$G$_{mo}$C$_{fs}$A$_{mo}$G$_{fs}$C$_{mo}$U$_{fs}$G$_{mo}$C$_{fs}$U$_{ms}$G$_{fs}$C$_{ms}$C$_{fs}$G$_{ms}$A$_{es}$A$_e$ | 9, 18 | 67.3 | 40 |

TABLE 4

Modified ssRNAs targeting Ataxin-3 CAG repeat region

| ISIS No. | Sequence 5'-3' | Mismatch Position from 5'-end | Tm, °C. (single strand) | Seq ID NO. |
|---|---|---|---|---|
| 618386 | 5'-Po-T$_{es}$C$_{fs}$U$_{mo}$G$_{fs}$C$_{mo}$U$_{fs}$G$_{mo}$C$_{fs}$A$_{mo}$G$_{fs}$C$_{mo}$U$_{fs}$G$_{mo}$C$_{fs}$A$_{ms}$G$_{fs}$C$_{ms}$U$_{fs}$G$_{ms}$A$_{es}$A$_e$ | 9, 15 | 87.1 | 35 |
| 641384 | 5'-Po-T$_{es}$C$_{fs}$U$_{mo}$G$_{fs}$C$_{mo}$U$_{fs}$G$_{mo}$C$_{fs}$A$_{mo}$G$_{fs}$C$_{mo}$U$_{fs}$G$_{mo}$C$_{fs}$C$_{ms}$G$_{fs}$C$_{ms}$U$_{fs}$G$_{ms}$A$_{es}$A$_e$ | 9, 15 | 62.8 | 39 |
| 618389 | 5'-Po-T$_{es}$C$_{fs}$U$_{mo}$G$_{fs}$C$_{mo}$U$_{fs}$G$_{mo}$C$_{fs}$A$_{mo}$G$_{fs}$C$_{mo}$U$_{fs}$G$_{mo}$C$_{fs}$U$_{ms}$G$_{fs}$C$_{ms}$A$_{fs}$G$_{ms}$A$_{es}$A$_e$ | 9, 18 | 79.6 | 38 |
| 641385 | 5'-Po-T$_{es}$C$_{fs}$U$_{mo}$G$_{fs}$C$_{mo}$U$_{fs}$G$_{mo}$C$_{fs}$A$_{mo}$G$_{fs}$C$_{mo}$U$_{fs}$G$_{mo}$C$_{fs}$U$_{ms}$G$_{fs}$C$_{ms}$C$_{fs}$G$_{ms}$A$_{es}$A$_e$ | 9, 18 | 67.3 | 40 |

TABLE 5

Modified ssRNAs having fewer phosphorothioate internucleoside linkages targeting the Ataxin-3 CAG repeat region

| ISIS No. | Sequence 5'-3' | Number of unmodified base | Seq ID NO |
|---|---|---|---|
| 553822 | 5'-Po-T$_{es}$C$_{fs}$U$_{mo}$G$_{fs}$C$_{mo}$U$_{fs}$G$_{mo}$C$_{fs}$A$_{mo}$G$_{fs}$C$_{mo}$U$_{fs}$G$_{mo}$C$_{fs}$U$_{ms}$G$_{fs}$C$_{ms}$U$_{fs}$G$_{ms}$A$_{es}$A$_e$ | 0 | 12 |
| 618202 | 5'-Po-T$_{es}$C$_{rs}$U$_{ro}$G$_{rs}$C$_{mo}$U$_{fs}$G$_{mo}$C$_{fs}$A$_{mo}$G$_{fs}$C$_{mo}$U$_{fs}$G$_{mo}$C$_{fs}$U$_{ms}$G$_{fs}$C$_{ms}$U$_{fs}$G$_{ms}$A$_{es}$A$_e$ | 3 | 12 |
| 618204 | 5'-Po-T$_{es}$C$_{fs}$U$_{mo}$G$_{fs}$C$_{mo}$U$_{fs}$G$_{mo}$C$_{rs}$A$_{ro}$G$_{rs}$C$_{mo}$U$_{fs}$G$_{mo}$C$_{fs}$U$_{ms}$G$_{fs}$C$_{ms}$U$_{fs}$G$_{ms}$A$_{es}$A$_e$ | 3 | 12 |
| 618205 | 5'-Po-T$_{es}$C$_{rs}$U$_{ro}$G$_{rs}$C$_{ro}$U$_{rs}$G$_{ro}$C$_{rs}$A$_{ro}$G$_{rs}$C$_{mo}$U$_{fs}$G$_{mo}$C$_{fs}$U$_{ms}$G$_{fs}$C$_{ms}$U$_{fs}$G$_{ms}$A$_{es}$A$_e$ | 9 | 12 |
| 618206 | 5'-Po-T$_{es}$C$_{fs}$U$_{mo}$G$_{fs}$C$_{mo}$U$_{fs}$G$_{mo}$C$_{fs}$A$_{mo}$G$_{fs}$C$_{ro}$U$_{rs}$G$_{ro}$C$_{rs}$U$_{rs}$G$_{rs}$C$_{rs}$U$_{rs}$G$_{rs}$A$_{es}$A$_e$ | 9 | 12 |
| 618209 | 5'-Po-T$_{es}$C$_{rs}$U$_{mo}$G$_{rs}$C$_{mo}$U$_{rs}$G$_{mo}$C$_{rs}$A$_{mo}$G$_{rs}$C$_{mo}$U$_{fs}$G$_{mo}$C$_{rs}$U$_{ms}$G$_{rs}$C$_{ms}$U$_{rs}$G$_{ms}$A$_{es}$A$_e$ | 9 | 12 |
| 618381 | 5'-Po-T$_{es}$C$_{ro}$U$_{ro}$G$_{ro}$C$_{mo}$U$_{fs}$G$_{mo}$C$_{fs}$A$_{mo}$G$_{fs}$C$_{mo}$U$_{fs}$G$_{mo}$C$_{fs}$U$_{ms}$G$_{fs}$C$_{ms}$U$_{fs}$G$_{ms}$A$_{es}$A$_e$ | 3 | 12 |
| 618382 | 5'-Po-T$_{es}$C$_{fs}$U$_{mo}$G$_{fo}$C$_{ro}$U$_{ro}$G$_{ro}$C$_{fs}$A$_{mo}$G$_{fs}$C$_{mo}$U$_{fs}$G$_{mo}$C$_{fs}$U$_{ms}$G$_{fs}$C$_{ms}$U$_{fs}$G$_{ms}$A$_{es}$A$_e$ | 3 | 12 |
| 618383 | 5'-Po-T$_{es}$C$_{fs}$U$_{mo}$G$_{fs}$C$_{mo}$U$_{fs}$G$_{mo}$C$_{ro}$A$_{ro}$G$_{ro}$C$_{mo}$U$_{fs}$G$_{mo}$C$_{fs}$U$_{ms}$G$_{fs}$C$_{ms}$U$_{fs}$G$_{ms}$A$_{es}$A$_e$ | 3 | 12 |
| 618384 | 5'-Po-T$_{es}$C$_{ro}$U$_{ro}$G$_{ro}$C$_{ro}$U$_{ro}$G$_{ro}$C$_{ro}$A$_{ro}$G$_{ro}$C$_{mo}$U$_{fs}$G$_{mo}$C$_{fs}$U$_{ms}$G$_{fs}$C$_{ms}$U$_{fs}$G$_{ms}$A$_{es}$A$_e$ | 9 | 12 |

Example 2

Modified Single Stranded RNAs (ssRNAs) Targeting Ataxin-3 (ATXN-3) CAG Repeat Region

A modified ssRNA from Table 1, ISIS 537775 was tested for its ability to selectively inhibit mutant ATXN-3 protein expression levels. The modified ssRNA was tested in the GM06151 cell line (74 CAG repeats mutant/24 CAG repeats wild-type) as described above. Cultured GM06151 cells at a density of 70,000 cells per well were transfected using lipid RNAiMAX (Invitrogen) with 0, 1, 3, 6, 12.5, 25, 50, and 100 nM concentrations of ISIS 537775 and samples were analyzed as described above.

ATXN-3 protein expression levels were analyzed and the IC$_{50}$ was calculated using methods as described previously. The IC$_{50}$ at which each oligonucleotide inhibits the mutant ATXN-3 protein expression is denoted as 'mut IC$_{50}$'. The IC$_{50}$ at which each oligonucleotide inhibits the wild-type ATXN-3 protein expression is denoted as 'wt IC$_{50}$'. Selectivity was calculated by dividing the IC$_{50}$ for inhibition of the wild-type ATXN-3 versus the $IC_{50}$ for inhibiting expression of the mutant ATXN-3 protein and the results are presented below.

As illustrated in Table 6, ISIS 537775 contained a mismatch at position 9, and achieved selectivity having an $IC_{50}$ of 3.6 nM for inhibition of the mutant ATXN-3 protein and an $IC_{50}$ of 20 nM for inhibition of the wild-type ATXN-3 protein resulting in approximately 6-fold selectivity of the mutant over the wild-type.

TABLE 6

Selectivity and Inhibition of ATXN-3 protein expression levels of modified ssRNAs

| RNA | ISIS NO. | mut IC50 (nM) | wt IC50 (nM) | Mismatch position | Selectivity (mut vs wt) | 5'- Chemistry |
|---|---|---|---|---|---|---|
| ss | 537775 | 8.7 | 22.9 | 9 | 3 | (E)-vinyl phosphonate |

Example 3

Modified Single Stranded RNAs (ssRNAs) Targeting Ataxin-3 (ATXN-3) CAG Repeat Region The modified ssRNAs ISIS 556886, ISIS 556887, ISIS 556888, ISIS 556889, ISIS 556890, ISIS 553822, ISIS 553821, ISIS 557407, ISIS 556891, ISIS 556892, ISIS 557406, ISIS 557408, 557409, ISIS 557426, ISIS 557427, ISIS 557428, ISIS 557429, and ISIS 557430 were selected and tested for their ability to selectively inhibit mutant ATXN-3 protein expression levels. The modified ssRNAs were tested in the GM06151 cell line (74 CAG repeats mutant/24 CAG repeats wild-type). Cultured GM06151 cells at a density of 70,000 cells per well were transfected using lipid RNAiMAX (Invitrogen) with 25 nM concentrations of ISIS 556886, ISIS 556887, ISIS 556888, ISIS 556889, ISIS 556890, ISIS 553822, ISIS 553821, ISIS 557407, ISIS 556891, ISIS 556892, ISIS 557406, ISIS 557408, 557409, ISIS 557426, ISIS 557427, ISIS 557428, ISIS 557429, and ISIS 557430 and samples were analyzed as described above.

ATXN-3 protein expression for both the mutant and wild-type were analyzed and are presented in Table 7 below. This example demonstrates that ISIS 556886, ISIS 556887, ISIS 556888, ISIS 556889, ISIS 556890, ISIS 553822, ISIS 553821, ISIS 557407, ISIS 556891, ISIS 556892, ISIS 557406, ISIS 557408, 557409, ISIS 557426, ISIS 557427, ISIS 557428, ISIS 557429, and ISIS 557430 selectively inhibit expression of the mutant ATXN-3 protein over wild-type ATXN-3 protein.

TABLE 7

Modified ssRNAs targeting Ataxin-3 CAG repeat region

| ISIS No. | % Expression of Mutant Ataxin-3 | % Expression of Wild-type Ataxin-3 | Mismatch Position from 5'-end |
|---|---|---|---|
| Control | 100 | 100 | |
| 556886 | 18 | 73 | 4 |
| 556887 | 6 | 50 | 5 |
| 556888 | 57 | 100 | 6 |
| 556889 | 16 | 72 | 7 |
| 556890 | 10 | 59 | 8 |
| 553822 | 7 | 83 | 9 |
| 553821 | 34 | 94 | 10 |
| 557407 | 48 | 100 | 10 |
| 556891 | 52 | 100 | 11 |
| 556892 | 38 | 99 | 12 |
| 557406 | 25 | 76 | 13 |
| 557408 | 16 | 70 | 16 |
| 557409 | 39 | 84 | 9, 10 |
| 557426 | 28 | 74 | 9, 10, 11 |
| 557427 | 52 | 82 | 8, 9, 10, 11 |
| 557428 | 102 | 115 | 4, 10, 16 |
| 557429 | 109 | 126 | 3, 8, 13, 17 |
| 557430 | 22 | 54 | None |

Example 4

Modified Single Stranded RNAs (ssRNAs) of Varying Length Targeting Ataxin-3 (ATXN-3) CAG Repeat Region The modified ssRNAs ISIS 553822, ISIS 581440, ISIS 581441, ISIS 581449, ISIS 581450, ISIS 581444, and ISIS 581445 were selected and tested for their ability to selectively inhibit mutant ATXN-3 protein expression levels. The modified ssRNAs were tested in the GM06151 cell line (74 CAG repeats mutant/24 CAG repeats wild-type). Cultured GM06151 cells at a density of 70,000 cells per well were transfected using lipid RNAiMAX (Invitrogen) with 25 nM concentrations of ISIS 553822, ISIS 581440, ISIS 581441, ISIS 581449, ISIS 581450, ISIS 581444, and ISIS 581445 and samples were analyzed as described above.

ATXN-3 protein expression for both the mutant and wild-type were analyzed and are presented in Table 8 below. This example demonstrates that ISIS 553822, ISIS 581440, ISIS 581441, ISIS 581449, ISIS 581450, ISIS 581444, and ISIS 581445 selectively inhibit expression of the mutant ATXN-3 protein over wild-type ATXN-3 protein.

TABLE 8

Modified ssRNAs of varying lengths targeting Ataxin-3 CAG repeat region

| ISIS No. | % Expression of Mutant Ataxin-3 | % Expression of Wild-type Ataxin-3 | Length |
|---|---|---|---|
| Control | 100 | 100 | NA |
| 553822 | 13 | 78 | 21 |
| 581440 | 17 | 83 | 20 |
| 581441 | 47 | 84 | 19 |
| 581449 | 39 | 86 | 18 |
| 581450 | 74 | 91 | 17 |
| 581444 | 86 | 93 | 16 |
| 581445 | 82 | 80 | 15 |

Example 5

Modified Single Stranded RNAs (ssRNAs) of Varying Length Targeting Ataxin-3 (ATXN-3) CAG Repeat Region ISIS 581440 was tested in the GM06151 cell line (74 CAG repeats mutant/24 CAG repeats wild-type) as described above. Cultured GM06151 cells at a density of 70,000 cells per well were transfected using lipid RNAiMAX (Invitrogen) with 0, 1, 3, 6, 12.5, 25, 50, and 100 nM concentrations of ISIS 581440 and samples were analyzed as described above. The effect of increasing concentrations of ISIS 581440 on the expression of ATXN-3 protein levels are presented in Table 9 below. This example demonstrates that ISIS 581440 selectively inhibits expression of the mutant APCN-3 protein compared to the wild-type APCN-3 protein in a dose-dependent fashion.

TABLE 9

Effect of increasing concentrations of ISIS 581440 on the expression of ATXN-3 protein levels

| ISIS No. | Concentration (nM) | % Expression of Mutant Ataxin-3 | % Expression of Wild-type Ataxin-3 |
|---|---|---|---|
| 553822 | 0 | 100 | 100 |
|  | 1 | 76 | 85 |
|  | 3 | 67 | 80 |
|  | 6 | 63 | 80 |
|  | 12 | 51 | 69 |
|  | 25 | 28 | 59 |
|  | 50 | 20 | 58 |
|  | 100 | 11 | 55 |

Example 6

Modified Single Stranded RNAs (ssRNAs) Having Mismatched Bases Targeting Ataxin-3 (ATXN-3) CAG Repeat Region The modified ssRNAs ISIS 553822, ISIS 641381, ISIS 641382, ISIS 641383, ISIS 618385, ISIS 618386, ISIS 618387, ISIS 618388, and ISIS 618389 were selected and tested for their ability to selectively inhibit mutant ATXN-3 protein expression levels. The modified ssRNAs were tested in the GM06151 cell line (74 CAG repeats mutant/24 CAG repeats wild-type). Cultured GM06151 cells at a density of 70,000 cells per well were transfected using lipid RNAiMAX (Invitrogen) with 25 nM concentrations of ISIS 553822, ISIS 641381, ISIS 641382, ISIS 641383, ISIS 618385, ISIS 618386, ISIS 618387, ISIS 618388, and ISIS 618389 and samples were analyzed as described above.

ATXN-3 protein expression for both the mutant and wild-type were analyzed and are presented in Table 10 below. This example demonstrates that ISIS 553822, ISIS 641381, ISIS 641382, ISIS 641383, ISIS 618385, ISIS 618386, ISIS 618387, ISIS 618388, and ISIS 618389 selectively inhibit expression of the mutant ATXN-3 protein over wild-type ATXN-3 protein.

TABLE 10

Modified ssRNAs targeting Ataxin-3 CAG repeat region

| ISIS No. | % Expression of Mutant Ataxin-3 | % Expression of Wild-type Ataxin-3 | Mismatch Position from 5'-end |
|---|---|---|---|
| Control | 100 | 100 | NA |
| 553822 | 11 | 63 | 9 |
| 641381 | 15 | 43 | 9, 11 |
| 641382 | 65 | 119 | 9, 12 |
| 641383 | 12 | 76 | 9, 13 |
| 618385 | 18 | 75 | 9, 14 |
| 618386 | 112 | 110 | 9, 15 |
| 618387 | 9 | 43 | 9, 16 |
| 618388 | 8 | 40 | 9, 17 |
| 618389 | 108 | 106 | 9, 18 |

Example 7

Modified Single Stranded RNAs (ssRNAs) of Varying Length Targeting Ataxin-3 (ATXN-3) CAG Repeat Region ISIS 618385 was tested in the GM06151 cell line (74 CAG repeats mutant/24 CAG repeats wild-type) as described above. Cultured GM06151 cells at a density of 70,000 cells per well were transfected using lipid RNAiMAX (Invitrogen) with 0, 0.5, 1, 3, 6, 12.5, 25, and 50 nM concentrations of ISIS 618385 and samples were analyzed as described above. The effect of increasing concentrations of ISIS 618385 on the expression of ATXN-3 protein levels are presented in Table 11 below. This example demonstrates that ISIS 618385 inhibits expression of ATXN-3 protein in a dose-dependent fashion.

TABLE 11

Effect of increasing concentrations of ISIS 618385 on the expression of ATXN-3 protein levels

| ISIS No. | Concentration (nM) | % Expression of Mutant Ataxin-3 | % Expression of Wild-type Ataxin-3 |
|---|---|---|---|
| 618385 | 0 | 100 | 100 |
|  | 0.5 | 72 | 95 |
|  | 1 | 57 | 94 |
|  | 3 | 32 | 89 |
|  | 6 | 19 | 85 |
|  | 12 | 11 | 79 |
|  | 25 | 16 | 71 |
|  | 50 | 3 | 62 |

Example 8

Modified Single Stranded RNAs (ssRNAs) Having Mismatched Bases Targeting Ataxin-3 (ATXN-3) CAG Repeat Region The modified ssRNAs ISIS 618386, ISIS 641384, ISIS 618389, and ISIS 641385 were selected and tested for their ability to selectively inhibit mutant ATXN-3 protein expression levels. The modified ssRNAs were tested in the GM06151 cell line (74 CAG repeats mutant/24 CAG repeats wild-type). Cultured GM06151 cells at a density of 70,000 cells per well were transfected using lipid RNAiMAX (Invitrogen) with 25 nM concentrations of ISIS 618386, ISIS 641384, ISIS 618389, and ISIS 641385 and samples were analyzed as described above.

ATXN-3 protein expression for both the mutant and wild-type were analyzed and are presented in Table 10 below. This example demonstrates that ISIS 618386, ISIS 641384, ISIS 618389, and ISIS 641385 selectively inhibit expression of the mutant APCN-3 protein over wild-type APCN-3 protein.

TABLE 12

| ISIS No. | % Expression of Mutant Ataxin-3 | % Expression of Wild-type Ataxin-3 | Mismatch Position from 5'-end |
|---|---|---|---|
| Control | 100 | 100 | NA |
| 618386 | 86 | 95 | 9, 15 |
| 641384 | 13 | 38 | 9, 15 |
| 618389 | 93 | 104 | 9, 18 |
| 641385 | 9 | 54 | 9, 18 |

Example 9

Modified Single Stranded RNAs (ssRNAs) Having Chemical Modifications Targeting Ataxin-3 (ATXN-3) CAG Repeat Region The modified ssRNAs ISIS 553822, ISIS 618202, ISIS 6182042, ISIS 618205, ISIS 618206, ISIS 618209, ISIS 618381, ISIS 618382, ISIS 618383, and ISIS 618384 were selected and tested for their ability to selectively inhibit mutant ATXN-3 protein expression levels. The modified ssRNAs were tested in the GM06151 cell line (74 CAG repeats mutant/24 CAG repeats wild-type). Cultured GM06151 cells at a density of 70,000 cells per well were transfected using lipid RNAiMAX (Invitrogen) with 25 nM concentrations of ISIS 553822, ISIS 618202, ISIS 6182042, ISIS 618205, ISIS 618206, ISIS 618209, ISIS 618381, ISIS 618382, ISIS 618383, and ISIS 618384 and samples were analyzed as described above.

ATXN-3 protein expression for both the mutant and wild-type were analyzed and are presented in Table 10 below.

TABLE 13

Modified ssRNAs targeting Ataxin-3 CAG repeat region

| ISIS No. | % Expression of Mutant Ataxin-3 | % Expression of Wild-type Ataxin-3 | Number of Unmodified Bases |
|---|---|---|---|
| Control | 100 | 100 | NA |
| 553822 | 1 | 39 | 0 |
| 618202 | 7 | 51 | 3 |
| 618204 | 2 | 37 | 3 |
| 618205 | 4 | 33 | 9 |
| 618206 | 20 | 54 | 9 |
| 618209 | 1 | 25 | 9 |
| ss-siRNAs with fewer PS linkages | | | |
| 618381 | 45 | 48 | 3 |
| 618382 | 14 | 86 | 3 |
| 618383 | 67 | 50 | 3 |
| 618384 | 39 | 101 | 9 |

Example 10

Dose-Response Study of Modified Single Stranded RNAs (ssRNAs) Having Chemical Modifications Targeting Ataxin-3 (ATXN-3) CAG Repeat Region ISIS 618202 and ISIS 618204 were tested in the GM06151 cell line (74 CAG repeats mutant/24 CAG repeats wild-type) as described above. Cultured GM06151 cells at a density of 70,000 cells per well were transfected using lipid RNAiMAX (Invitrogen) with 0, 0.5, 1, 3, 6, 12.5, 25, and 50 nM concentrations of ISIS 618385 and samples were analyzed as described above. The effect of increasing concentrations of ISIS 618385 on the expression of ATXN-3 protein levels are presented in Table 11 below. This example demonstrates that ISIS 618202 and ISIS 618204 inhibit expression of ATXN-3 protein in a dose-dependent fashion.

TABLE 14

Effect of increasing concentrations of ISIS 618385 on the expression of ATXN-3 protein levels

| ISIS No. | Concentration (nM) | % Expression of Mutant Ataxin-3 | % Expression of Wild-type Ataxin-3 |
|---|---|---|---|
| 618202 | 0 | 100 | 100 |
| | 0.5 | 93 | 96 |
| | 1 | 88 | 94 |
| | 3 | 71 | 90 |
| | 6 | 56 | 87 |
| | 12 | 40 | 83 |
| | 25 | 25 | 77 |
| | 50 | 14 | 71 |
| 618204 | 0 | 100 | 100 |
| | 0.5 | 79 | 89 |
| | 1 | 69 | 86 |
| | 3 | 50 | 79 |
| | 6 | 38 | 74 |
| | 12 | 27 | 68 |
| | 25 | 17 | 61 |
| | 50 | 11 | 53 |

Example 11 ss-siRNAs can Induce Alternative Splicing

GM06151 fibroblasts were treated with either ISIS 557426 (the "426 compound") or a negative control (CM). After treatment with ISIS 557426, PCR analysis confirmed that treatment with ISIS 557426 induced ATXN3 exon 10 exclusion (See FIG. 1).

Figure 3A:
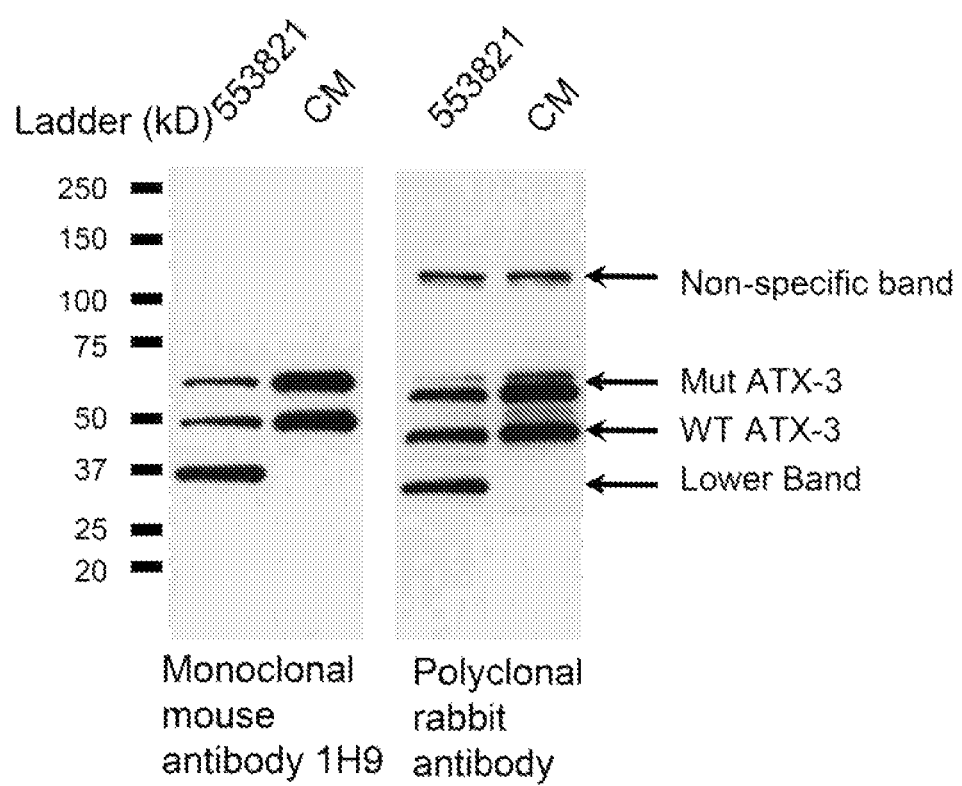
FIG. 3a shows the presence of a low molecular weight band at approximately 35 kDa after treatment with the ss-siRNA ISIS 553821 as detected by either a monoclonal mouse antibody 1H9 or a polyclonal rabbit antibody.
Figure 3B:
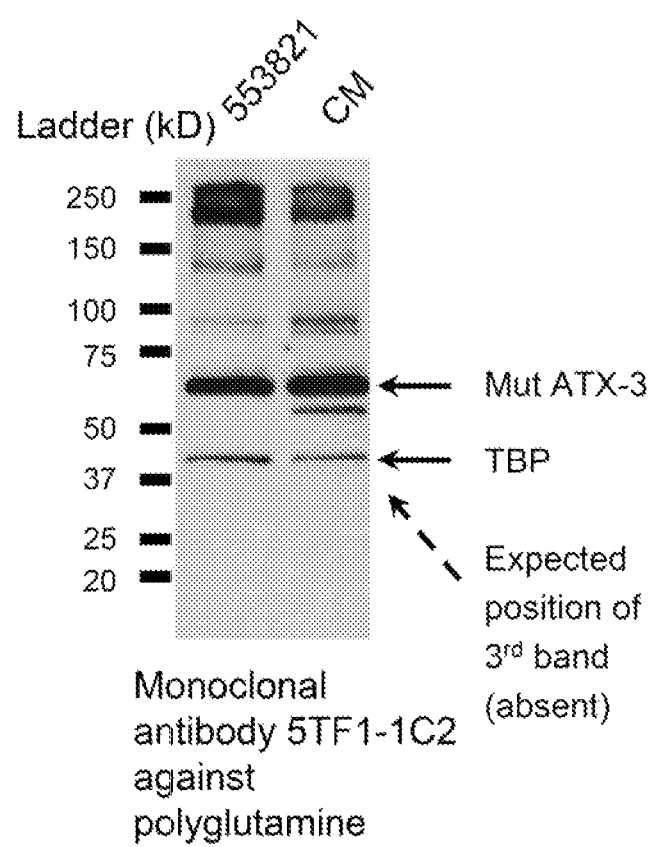
FIG. 3b shows the absence of the same low molecular weight band in the presence of the monoclonal antibody 5Tf1-1C2. The monoclonal antibody 5Tf1-1C2 detects polyglutamate repeats.

GM06151 fibroblasts were also treated with either ISIS 553821 or a negative control (CM). After treatment with ISIS 557426, PCR analysis confirmed that treatment with ISIS 557426 produced the presence of a low molecular weight band at 35 kDa, indicating that the band is a shorter fragment of ATXN-3 without the polyglutamine repeat. Treatment with a negative control did not produce the presence of a low molecular weight band at 35 kDa (See FIG. 3a). Additionally, antibody 5TF1-1C2, which specifically detects regions of expanded polyglutamines did not detect the lower molecular weight band, indicating that the product does not include the expanded repeat (See FIG. 3b).

Example 12

PNA and BNA Compounds can Induce Alternative Splicing

Figure 4:
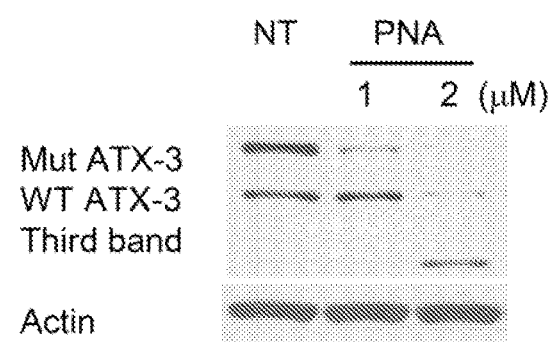
FIG. 4a shows the presence of a third band after treatment with a PNA compound (PNA).
FIG. 4b shows the presence of a $3^{rd}$ band after treatment with a number of BNA compounds. In both FIG. 4a and FIG. 4b, no treatment (NT) did not produce a third band.
Figure 4:
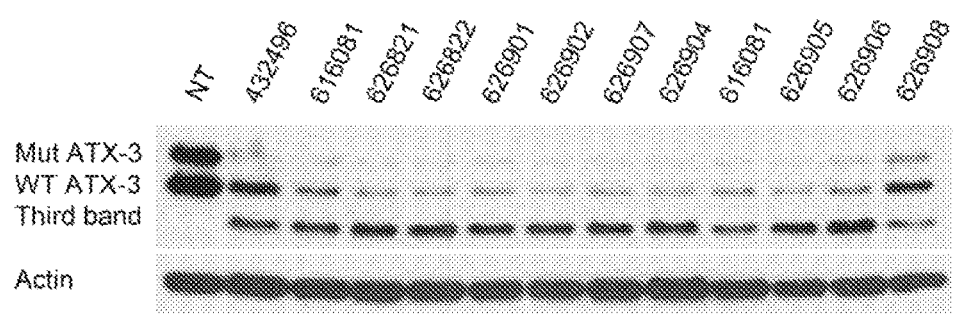

GM06151 fibroblasts were treated with either a PNA compound ISIS 557426 or received no treatment (NT). Further GM06151 fibroblasts were treated with either a BNA compound displayed in Table 15 below, or received no treatment (NT). Both the PNA compound and the BNA compounds in the table below do not function through the RNAi pathway and do not activate RNaseH. Treatment with the PNA compound and the BNA compounds caused the formation of a third band, indicating that the presence of the third band is caused by steric blocking of the splicing machinery rather than operation of the RNAi or RNAse H mechanism (See FIGS. 4a and 4b).

Modified PNA and BNA compounds are described in the tables below. A subscript "s" between two nucleosides indicates a phosphorothioate internucleoside linkage (going 5' to 3'). A subscript "o" between two nucleosides indicates a phosphodiester internucleoside linkage (going 5' to 3'). Nucleosides without a subscript are β-D-2'-deoxyribonucleosides. Nucleosides followed by a subscript "k", "f", "m" or "e" are sugar modified nucleosides. A subscript "f" indicates a 2'-fluoro modified nucleoside, a subscript "m" indicates a 2'-O-methyl modified nucleoside, a subscript "k" indicates a cEt "constrained ethyl" modified nucleoside (a BNA modified nucleoside), and a subscript "e" indicates a 2'-O-methoxyethyl (MOE) modified nucleoside. $^{me}C$ indicates a 5-methyl cytosine nucleoside. Underlined nucleosides indicate the mismatch position.

TABLE 15

PNA and BNA Compounds

| ISIS No. | Sequence 5'-3' | Chemistry | SEQ ID NO |
|---|---|---|---|
| 432496 | $G_{ds}C_{ks}U_{ks}G_{ds}C_{ds}U_{ks}G_{ds}C_{ds}U_{ks}G_{ds}C_{ds}U_{ks}G_{ds}C_{ds}U_{ks}G_{ds}C_{ds}U_{ks}G_{d}$ | PNA | 41 |
| 616081 | $G_{ds}{}^mC_{ds}T_{ks}G_{ds}{}^mC_{ds}T_{ks}G_{ds}{}^mC_{ds}T_{ks}G_{ds}{}^mC_{ds}T_{ks}G_{ds}{}^mC_{ds}T_{ks}G_{ds}{}^mC_{ds}T_{ks}G_{d}$ | BNA | 42 |
| 626821 | $G_{ks}{}^mC_{ds}T_{ks}G_{ds}{}^mC_{ds}T_{ks}G_{ds}{}^mC_{ds}T_{ks}G_{ds}{}^mC_{ds}T_{ks}G_{ds}{}^mC_{ds}T_{ks}G_{ds}{}^mC_{ds}T_{ks}G_{k}$ | BNA | 42 |
| 626822 | $G_{ks}{}^mC_{ds}T_{ks}G_{ds}{}^mC_{ks}T_{s}G_{ks}{}^mC_{ds}T_{ks}G_{ds}{}^mC_{ks}T_{s}G_{ks}{}^mC_{ds}T_{ks}G_{ds}{}^mC_{ks}T_{ds}G_{k}$ | BNA | 42 |
| 626901 | ${}^mC_{ks}T_{ds}G_{ks}{}^mC_{ds}T_{ds}G_{ks}{}^mC_{ds}T_{s}G_{ks}{}^mC_{ds}T_{s}G_{ks}{}^mC_{ds}T_{ds}G_{ks}{}^mC_{ds}T_{ds}G_{ks}{}^mC_{k}$ | BNA | 43 |
| 626902 | ${}^mC_{ks}T_{ds}G_{ks}{}^mC_{ds}T_{ks}G_{ds}{}^mC_{ks}T_{ds}G_{ks}{}^mC_{ds}T_{ks}G_{ds}{}^mC_{ks}T_{s}G_{ks}{}^mC_{ds}T_{ks}G_{ds}{}^mC_{ks}$ | BNA | 43 |
| 626907 | $T_{ks}G_{ds}{}^mC_{ks}T_{s}G_{ks}{}^mC_{ds}T_{s}G_{ks}{}^mC_{ds}T_{s}G_{ks}{}^mC_{ds}T_{s}G_{ks}{}^mC_{ds}T_{ds}G_{ds}{}^mC_{ks}T_{k}$ | BNA | 44 |
| 626904 | $T_{ks}G_{ds}{}^mC_{ks}T_{s}G_{ks}{}^mC_{ds}T_{ks}G_{ds}{}^mC_{ks}T_{s}G_{ks}{}^mC_{ds}T_{ks}G_{ds}{}^mC_{ks}T_{ds}G_{ks}G_{ds}{}^mC_{k}$ | BNA | 45 |

BNA with less phosphorothioate linkages

| 626905 | $G_{ks}{}^mC_{ds}T_{ko}G_{ds}{}^mC_{ds}T_{ko}G_{ds}{}^mC_{ds}T_{ko}G_{ds}{}^mC_{ds}T_{ko}G_{ds}{}^mC_{ds}T_{ko}G_{ds}{}^mC_{ds}T_{ks}G_{k}$ | BNA | 42 |
| 626906 | ${}^mC_{ks}T_{ds}G_{ko}{}^mC_{ds}T_{ds}G_{ko}{}^mC_{ds}T_{ds}G_{ko}{}^mC_{ds}T_{s}G_{ko}{}^mC_{ds}T_{ds}G_{ko}{}^mC_{ds}T_{ds}G_{ks}{}^mC_{k}$ | BNA | 43 |
| 626908 | $T_{ks}G_{ds}{}^mC_{ko}T_{s}G_{ds}{}^mC_{ko}T_{s}G_{ds}{}^mC_{ko}T_{s}G_{ds}{}^mC_{ko}T_{s}G_{ds}{}^mC_{ko}T_{ds}G_{ds}{}^mC_{ks}T_{k}$ | BNA | 44 |

Example 13

Allele-selective Inhibition of Mutant Atrophin-1 Expression by Single-Stranded RNAs (ss-siRNAs)

To determine whether ss-siRNAs could inhibit expression of Atrophin-1 ("ATN-1") in an allele-selective manner, a series of ss-siRNAs that varied in the position and number of mismatched bases were tested in vitro (see Table 16 below). To evaluate allele-selective silencing of ATN-1 a fibroblast cell line derived from DRPLA patient cells (GM13716) was used. GM13716 cells are heterozygous for mutant ATN-1 and contain 16 wild-type CAG repeats and 68 mutant repeats.

DRPLA patient-derived fibroblast cell lines GM13716 were obtained from the Coriell Institute (Camden, N.J.). The fibroblasts were maintained at 37° C. and 5% $CO_2$ in Minimal Essential Media Eagle (MEM) (Sigma, M4655) supplemented with 15% heat inactivated fetal bovine serum (Sigma) and 0.5% MEM nonessential amino acids (Sigma). Cells were plated at a density of 80,000 per well of a 6-well plate 48 h before transfection. Cells were typically harvested 2 days after transfection for protein assay. The ss-siRNAs were transfected into cells and harvested 2 days after transfection for protein assay.

Mutant and wild-type ATN-1 from GM13716 cells were separated by polyacrylamide gel electrophoresis (SDS-PAGE) and analyzed by western blot analysis. Tris-HCl SDS-PAGE was used to separate ATN-1 isoforms [separating gel: 5% acrylamide-bisacrylamide (49:1), 450 mM Tris-HCl pH 8.8, 0.1% SDS; stacking gel 4% acrylamide-bisacrylamide (49:1), 150 mM Tris-HCl pH 6.8; running buffer: Tris/Glycine/SDS buffer (BioRad)]. Gels were run at 75V for 15 minutes, then 120V for 60 minutes (Put the electrophoresis tank in ice-water and keep the temperature of inner part of the tank around 25° C.). The primary antibodies were used: anti-ATN1 (A300-753A, Bethyl, 1:1000), and anti-β-actin (Sigma, 1:10000). Protein bands were quantified using ImageJ software. The percentage of inhibition was calculated as a relative value to a control sample. Dose fitting curve was generated using GraphPad Prism 6 program by the equation: y=100(1−xm/(nm+xm)), where y is percentage of inhibition and x is the siRNA concentration, n is the IC50 value, and m is the Hill coefficient value. Selectivity (fold) was then calculated using the $IC_{50}$ values for the mutant and wilt-type cells. This example demonstrates that ss-siRNA compounds selectivity reduce expression of a CAG expanded mutant allele compared to a wild type allele having fewer CAG repeats.

TABLE 16

Allele-selective inhibition of mutant Atrophin-1 expression by single-stranded RNAs

| ISIS No. | Sequence 5'-3' | Mut $IC_{50}$ (nM) | WT $IC_{50}$ (nM) | Selectivity (fold) |
|---|---|---|---|---|
| 537775 | 5'-Pv-$T_{es}C_{fs}U_{m}G_{fs}C_{m}U_{fs}G_{m}C_{fs}A_{m}G_{fs}C_{m}U_{fs}G_{m}C_{fs}U_{ms}G_{fs}C_{ms}U_{fs}G_{ms}A_{es}A_{e}$-3' | 1.1 | >25 | >22.7 |
| 553822 | 5'-Po-$T_{es}C_{fs}U_{mo}G_{fs}C_{mo}U_{fs}G_{mo}C_{fs}A_{mo}G_{fs}C_{mo}U_{fs}G_{mo}C_{fs}U_{ms}G_{fs}C_{ms}U_{fs}G_{ms}A_{es}A_{e}$ | 1.9 | >25 | 13.4 |
| 557426 | 5'-Po-$T_{es}C_{fs}U_{mo}G_{fs}C_{mo}U_{fs}G_{mo}C_{fs}A_{mo}A_{fs}A_{mo}U_{fs}G_{mo}C_{fs}U_{ms}G_{fs}C_{ms}U_{fs}G_{ms}A_{es}A_{e}$ | 1.7 | >25 | >14.7 |
| 641381 | 5'-Po-$T_{es}C_{fs}U_{mo}G_{fs}C_{mo}U_{fs}G_{mo}C_{fs}A_{mo}G_{fs}A_{mo}U_{fs}G_{mo}C_{fs}U_{ms}G_{fs}C_{ms}U_{fs}G_{ms}A_{es}A_{e}$ | 2.4 | >25 | 10.4 |

TABLE 16-continued

Allele-selective inhibition of mutant Atrophin-1 expression by single-stranded RNAs

| ISIS No. | Sequence 5'-3' | Mut IC$_{50}$ (nM) | WT IC$_{50}$ (nM) | Selectivity (fold) |
|---|---|---|---|---|
| 641383 | 5'-Po-T$_{es}$C$_{fs}$U$_{mo}$G$_{fs}$C$_{mo}$U$_{fs}$G$_{mo}$C$_{fs}$A$_{mo}$G$_{fs}$C$_{mo}$U$_{fs}$A$_{mo}$C$_{fs}$U$_{ms}$G$_{fs}$C$_{ms}$U$_{fs}$G$_{ms}$A$_{es}$A$_e$ | 3.1 | 16.3 | 5.3 |
| 618385 | 5'-Po-T$_{es}$C$_{fs}$U$_{mo}$G$_{fs}$C$_{mo}$U$_{fs}$G$_{mo}$C$_{fs}$A$_{mo}$G$_{fs}$C$_{mo}$U$_{fs}$G$_{mo}$A$_{fs}$U$_{ms}$G$_{fs}$C$_{ms}$U$_{fs}$G$_{ms}$A$_{es}$A$_e$ | 3.0 | 8.5 | 2.8 |
| 641384 | 5'-Po-T$_{es}$C$_{fs}$U$_{mo}$G$_{fs}$C$_{mo}$U$_{fs}$G$_{mo}$C$_{fs}$A$_{mo}$G$_{fs}$C$_{mo}$U$_{fs}$G$_{mo}$C$_{fs}$C$_{ms}$G$_{fs}$C$_{ms}$U$_{fs}$G$_{ms}$A$_{es}$A$_e$ | 1.2 | >25 | >20.5 |
| 618204 | 5'-Po-T$_{es}$C$_{fs}$U$_{mo}$G$_{fs}$C$_{mo}$U$_{fs}$G$_{mo}$C$_{rs}\underline{A}_{ro}$G$_{rs}$C$_{mo}$U$_{fs}$G$_{mo}$C$_{fs}$U$_{ms}$G$_{fs}$C$_{ms}$U$_{fs}$G$_{ms}$A$_{es}$A$_e$ | 1.1 | 14 | 12.7 |

In the table above, a subscript "s" between two nucleosides indicates a phosphorothioate internucleoside linkage (going 5' to 3'). The absence of a subscript "s" between two nucleosides indicates a phosphodiester internucleoside linkage. A "Pv" at the 5'-end indicates a 5'-(E)-vinylphosphonate group, (PO(OH)$_2$(CH=CH—). A "Po" at the 5'-end indicates a 5'-phosphate group, (PO(OH)$_2$—). Nucleosides without a subscript are β-D-2'-deoxyribonucleosides. Nucleosides with an "r" subscript are ribonucleosides. Nucleosides followed by a subscript "f", "m" or "e" are sugar modified nucleosides. A subscript "f" indicates a 2'-fluoro modified nucleoside, a subscript "m" indicates a 2'-O-methyl modified nucleoside and a subscript "e" indicates a 2'-O-methoxyethyl (MOE) modified nucleoside. $^{me}$C indicates a 5-methyl cytosine nucleoside. Unless otherwise indicated, underlined nucleosides indicate the mismatch position. In the table above, ISIS No. 553822 has a mismatch at position 9. ISIS No. 557426 has a mismatch at position 9, 10, and 11. ISIS No. 641381 has a mismatch at position 9 and 13. ISIS No. 641383 has a mismatch at position 9 and 13. ISIS No. 618385 has a mismatch at position 9 and 14. ISIS No. 618384 has a mismatch at position 9 and 15. ISIS No. 618204 has a mismatch at position 9.

The invention claimed is:
1. A method of modulating the splicing of an ataxin-3 pre-mRNA containing at least one expanded repeat, comprising contacting a cell with a compound comprising a modified single-stranded RNA oligonucleotide consisting of 13 to 30 linked nucleosides and having a nucleobase sequence complementary to a repeat region of the ataxin-3 pre-mRNA, wherein the 5'-terminal nucleoside of the modified single-stranded RNA oligonucleotide comprises a phosphate moiety and an internucleoside linking group linking the 5'-terminal nucleoside to the remainder of the modified single-stranded RNA oligonucleotide, wherein the modified single-stranded RNA oligonucleotide comprises a mismatch at the ninth nucleobase from the 5'-end of the modified single-stranded RNA oligonucleotide relative to a repeat region of the expanded repeat-containing target pre-mRNA.

2. The method of claim 1, wherein the 5'-terminal nucleoside of the modified single-stranded RNA oligonucleotide has Formula I:

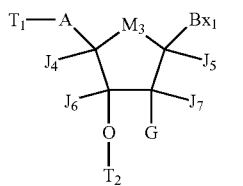

wherein:
T$_1$ is a phosphorus moiety;
T$_2$ is an internucleoside linking group linking the 5'-terminal nucleoside of Formula I to the remainder of the modified single-stranded RNA oligonucleotide;
A has a formula selected from among:

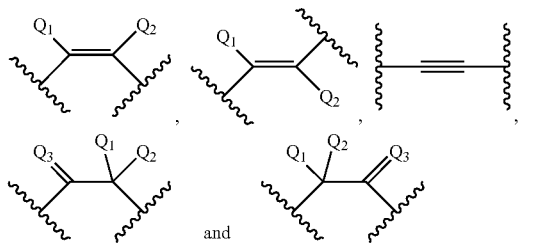

Q$_1$ and Q$_2$ are each independently selected from among: H, halogen, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl, substituted C$_2$-C$_6$ alkynyl, and N(R$_3$)(R$_4$);
Q$_3$ is selected from among: O, S, N(R$_5$), and C(R$_6$)(R$_7$);
each R$_3$, R$_4$ R$_5$, R$_6$ and R$_7$ is independently selected from among: H, C$_1$-C$_6$ alkyl, substituted C$_1$-C$_6$ alkyl, and C$_1$-C$_6$ alkoxy;
M$_3$ is selected from among: O, S, NR$_{14}$, C(R$_{15}$)(R$_{16}$), C(R$_{15}$)(R$_{16}$)C(R$_{17}$)(R$_{18}$), C(R$_{15}$)=C(R$_{17}$), OC(R$_{15}$)(R$_{16}$), and OC(R$_{15}$)(Bx$_2$);

R$_{14}$ is selected from among: H, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl, and substituted C$_2$-C$_6$ alkynyl;
R$_{15}$, R$_{16}$, R$_{17}$ and R$_{18}$ are each independently selected from among: H, halogen, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl, and substituted C$_2$-C$_6$ alkynyl;
if Bx$_2$ is present, then Bx$_2$ is a nucleobase and Bx$_1$ is selected from among: H, halogen, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl, and substituted C$_2$-C$_6$ alkynyl;
if Bx$_2$ is not present, then Bx$_1$ is a nucleobase;
either each of J$_4$, J$_5$, J$_6$ and J$_7$ is independently selected from among: H, halogen, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl, and substituted C$_2$-C$_6$ alkynyl;
or J$_4$ forms a bridge with one of J$_5$ or J$_7$ wherein the bridge comprises from 1 to 3 linked biradical groups selected from O, S, NR$_{19}$, C(R$_{20}$)(R$_{21}$), C(R$_{20}$)=C(R$_{21}$), C[=C(R$_{20}$)(R$_{21}$)] and C(=O) and the other two of J$_5$, J$_6$ and J$_7$ are independently selected from among: H, halogen, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl, and substituted C$_2$-C$_6$ alkynyl;
each R$_{19}$, R$_{20}$ and R$_{21}$ is independently selected from among: H, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl or substituted C$_2$-C$_6$ alkynyl;
G is selected from among: H, OH, halogen, O—[C(R$_8$)(R$_9$)]$_n$—[(C=O)$_m$—X$_1$]$_j$—Z, and a conjugate group;
each R$_8$ and R$_9$ is independently selected from among: H, halogen, C$_1$-C$_6$ alkyl, and substituted C$_1$-C$_6$ alkyl;
X$_1$ is O, S or N(E$_1$);
Z is selected from among: H, halogen, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl, and N(E$_2$)(E$_3$);
E$_1$, E$_2$ and E$_3$ are each independently selected from among: H, C$_1$-C$_6$ alkyl, and substituted C$_1$-C$_6$ alkyl;
n is from 1 to 6;
m is 0 or 1;
j is 0 or 1;
provided that, if j is 1, then Z is other than halogen or N(E$_2$)(E$_3$);
each substituted group comprises one or more optionally protected substituent groups independently selected from among: a halogen, OJ$_1$, N(J$_1$)(J$_2$), =NJ$_1$, SJ$_1$, N$_3$, CN, OC(=X$_2$)J$_1$, OC(=X$_2$)N(J$_1$)(J$_2$), and C(=X$_2$)N(J$_1$)(J$_2$);
X$_2$ is O, S or NJ$_3$; and
each J$_1$, J$_2$ and J$_3$ is independently selected from among: H and C$_1$-C$_6$ alkyl.

3. The method of claim 2, wherein $M_3$ is O.

4. The method of claim 2, wherein each of $J_4$, $J_5$, $J_6$ and $J_7$ is H.

5. The method of claim 2, wherein A has the formula:

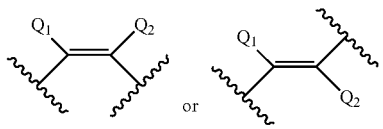

wherein:
$Q_1$ and $Q_2$ are each independently selected from among: H, halogen, $C_1$-$C_6$ alkyl, substituted $C_1$-$C_6$ alkyl, $C_1$-$C_6$ alkoxy, and substituted $C_1$-$C_6$ alkoxy.

6. The method of claim 2, wherein each of Q and $Q_2$ is H.

7. The method of claim 2, wherein $T_1$ has the formula:

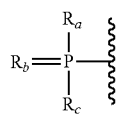

wherein:
$R_a$ and $R_c$ are each independently selected from among: hydroxyl, thiol, $C_1$-$C_6$ alkyl, substituted $C_1$-$C_6$ alkyl, $C_1$-$C_6$ alkoxy, substituted $C_1$-$C_6$ alkoxy, amino or substituted amino; and
$R_b$ is O or S.

8. The method of claim 2, wherein G is selected from among: a halogen, $OCH_3$, $OCF_3$, $OCH_2$ $CH_3$, $OCH_2$ $CF_3$, $OCH_2$—CH=$CH_2$, $O(CH_2)_2$—$OCH_3$, $O(CH_2)_2$—O($CH_2$)$_2$—N($CH_3$)$_2$, $OCH_2$ C(=O)—N(H)$CH_3$, $OCH_2$ C(=O)—N(H)—($CH_2$)$_2$—N($CH_3$)$_2$, and $OCH_2$—N(H)—C(=NH)$NH_2$.

9. The method of claim 2, wherein G is selected from among: F, $OCH_3$, and $O(CH_2)_2$—$OCH_3$.

10. The method of claim 2, wherein the 5'-terminal nucleoside has Formula V:

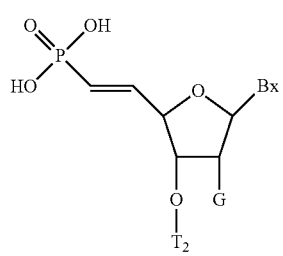

wherein:
Bx is selected from among: uracil, thymine, cytosine, 5-methyl cytosine, adenine, and guanine;

$T_2$ is a phosphorothioate internucleoside linking group linking the 5'-terminal nucleoside of Formula V to the remainder of the modified single-stranded RNA oligonucleotide; and G is selected from among: a halogen, $OCH_3$, $OCF_3$, $OCH_2$ $CH_3$, $OCH_2$ $CF_3$, $OCH_2$—CH=$CH_2$, $O(CH_2)_2$—$OCH_3$, $O(CH_2)_2$—O($CH_2$)$_2$—N($CH_3$)$_2$, $OCH_2$ C(=O)—N(H)$CH_3$, $OCH_2$ C(=O)—N (H)—($CH_2$)$_2$—N($CH_3$)$_2$, $OCH_2$—N(H)—C(=NH)$NH_2$, and a conjugate group.

11. The method of claim 1, wherein the remainder of the modified single-stranded RNA oligonucleotide comprises at least one region having sugar motif:

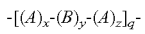

wherein
A is a modified nucleoside of a first type,
B is a modified nucleoside of a second type;
each x and each y is independently 1 or 2;
z is 0 or 1;
q is 1-15.

12. The method of claim 11, wherein the modifications of the first type and the modifications of the second type are selected from among: 2'-F, 2'-OMe, and F-HNA.

13. The method of claim 11, wherein the remainder of the modified single-stranded RNA oligonucleotide comprises 1-4 3'-terminal nucleosides, each comprising the same sugar modification, wherein the sugar modification of the 1-4 3'terminal nucleosides is different from the sugar modification of the immediately adjacent nucleoside.

14. The method of claim 1, wherein the modified single-stranded RNA oligonucleotide has two mismatches relative to a repeat region of the expanded repeat-containing target pre-mRNA.

15. The method of claim 1, wherein the modified single-stranded RNA oligonucleotide has three mismatches relative to a repeat region of the expanded repeat-containing target pre-mRNA.

16. The method of claim 15, wherein the mismatches are located at the $9^{th}$, $10^{th}$, and $11^{th}$ nucleobases from the 5'-end of the modified single-stranded RNA oligonucleotide.

17. The method of claim 1, wherein the cell is in an animal.

* * * * *